United States Patent
Nagele

(10) Patent No.: US 10,436,801 B2
(45) Date of Patent: Oct. 8, 2019

(54) EARLY STAGE PARKINSON'S DISEASE DIAGNOSTIC KITS AND METHODS

(71) Applicant: Rowan University, Glassboro, NJ (US)

(72) Inventor: Robert G. Nagele, Turnersville, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 15/041,573

(22) Filed: Feb. 11, 2016

(65) Prior Publication Data

US 2016/0231335 A1 Aug. 11, 2016

Related U.S. Application Data

(60) Provisional application No. 62/114,971, filed on Feb. 11, 2015.

(51) Int. Cl.
*G01N 33/68* (2006.01)
*G01N 33/564* (2006.01)

(52) U.S. Cl.
CPC ....... *G01N 33/6896* (2013.01); *G01N 33/564* (2013.01); *G01N 2800/2835* (2013.01)

(58) Field of Classification Search
CPC combination set(s) only.
See application file for complete search history.

(56) References Cited

U.S. PATENT DOCUMENTS

| | | |
|---|---|---|
| 2003/0068659 A1 | 4/2003 | Kilgannon et al. |
| 2014/0017303 A1 | 1/2014 | Navon et al. |
| 2014/0045915 A1 | 2/2014 | Skog et al. |
| 2014/0364328 A1 | 12/2014 | Nagele |

FOREIGN PATENT DOCUMENTS

| | | |
|---|---|---|
| WO | 2011072247 A2 | 6/2011 |
| WO | 2012045324 A1 | 4/2012 |
| WO | 2013122609 A1 | 8/2013 |
| WO | 2014009747 A1 | 1/2014 |
| WO | 2014001576 A2 | 1/2017 |

OTHER PUBLICATIONS

Life Technologies Corporation (product brochure), ProtoArray® Human Protein Microarrays: Absolute identification of novel auto-immune biomarkers, 2009.*
ProtoArray v5 content list (2010). Published online at <www.invitrogen.com> Retrieved on Nov. 25, 2016.*
Devos et al., Clinical Therap, 35(10):1640-1652, 2013.*
Riederer and Laux, Experimental Neurobiology, 2: 1-17, Mar. 2011.*
Han et al.,"Diagnosis of Parkinson's disease based on disease-specific autoantibody profiles in human sera," PLos ONe ePub (Feb. 22, 2012); 9(2):e3233.
Nagele et al., "Diagnosis of Alzheimer's disease based on disease-specific autoantibody profiles in human sera," PLoS One ePub Epub (Aug. 3, 2011): 6(8):e23112.
Nagele et l., "Brain reactive autoantibodies prevalent in human sera increase intraneuronal amyloid beta 1-42 deposition," J Alzheimers Dis (Apr. 2011): 25(4):605-622.
Yanamandra et al., "a-synuclein reactive antibodies as diagnositc biomarkers in blood sera of Parkinson's desiease patients," PLoS One (Apr. 25, 2011); 6(4):e18513.

* cited by examiner

*Primary Examiner* — Kimberly Ballard
*Assistant Examiner* — Stacey N MacFarlane
(74) *Attorney, Agent, or Firm* — Saul Ewing Arnstein & Lehr LLP; Domingos J. Silva

(57) ABSTRACT

The present invention relates to diagnostic methods, reagents, and kits for detecting and diagnosing Early Stage Parkinson's disease.

11 Claims, 5 Drawing Sheets

Specification includes a Sequence Listing.

EARLY STAGE PARKINSON'S DISEASE DIAGNOSTIC KITS AND METHODS

RELATED APPLICATIONS

This application claims priority to U.S. Provisional 62/114,971, filed Feb. 11, 2015, the content of which is incorporated herein in its entirety.

FIELD OF THE INVENTION

This invention relates to the diagnosis of early-stage Parkinson's disease (PD) using autoantibodies as blood-based biomarkers.

BACKGROUND OF THE INVENTION

PD is the second most common neurodegenerative disease worldwide and affects more than one percent of people older than sixty years of age and roughly four percent of those older than 85 (de Lau et al. *The Lancet Neurology* 5, 525-535 (2006)). Currently, there is no simple and reliable diagnostic test for PD. It remains essentially a clinical diagnosis, subject to variations in patient presentation and physician awareness. Upon post-mortem examination, it has been estimated that only 80% of patients clinically diagnosed with PD have typical post-mortem neuropathological changes (Hughes et al. *Archives of neurology* 50, 140-148 (1993)). Even in subjects with an apparently positive response to dopaminergic medication, a clinical diagnosis of PD can have relatively poor accuracy (Adler et al. *Neurology* 83, 406-412 (2014)). Results are far worse for very Early-Stage PD subjects (Adler et al. *Neurology* 82, 858-864 (2014)). Neuroimaging approaches such as DaT scanning have some utility, but are expensive, invasive, and not very specific. Detection of biomarkers in the cerebrospinal fluid (CSF) or blood, presumably associated with PD pathogenesis, such as alpha-synuclein or DJ-1, has so far failed to yield consistent results (Hong et al. *Brain: a journal of neurology* 133, 713-726 (2010), Gerlach et al. *Journal of neural transmission* 119, 39-52 (2012), van Dijk et al. *European journal of neurology: the official journal of the European Federation of Neurological Societies* 21, 388-394 (2014), Mollenhauer et al. *Experimental neurology* 213, 315-325 (2008), and Aerts et al. *Neurobiology of aging* 33, 430 e431-433 (2012). Thus, there remains a great need for an accurate, inexpensive, and noninvasive test that can detect PD in its earliest stages.

SUMMARY OF INVENTION

This invention relates to a diagnosis of Early-Stage PD using autoantibodies as blood-based biomarkers.

In some embodiments, the present invention provides a method of identifying a subject that has or is at risk of developing Early-Stage PD comprising obtaining an immunoglobulin-containing biological sample from the subject, performing an assay to determine the presence or absence of at least one Early-Stage PD autoantibody biomarker in the biological sample, and identifying the subject who has or is at risk for developing Early-Stage PD if at least one Early-Stage PD autoantibody biomarker is present. Each of the Early-Stage PD autoantibody biomarkers is an autoantibody that specifically binds to at least one target selected from the group consisting of the target antigens listed in Table 1.

In some embodiments, the assay can be performed by a process comprising contacting the immunoglobulin-containing sample with at least one target antigen or an epitope thereof under conditions that allow formation of an immunocomplex between (i) the antigen or an epitope thereof and (ii) the autoantibody biomarker, and detecting the presence or absence of the immunocomplex. The presence of the immunocomplex is indicative of the presence of the biomarker and the disease and wherein the absence of an immunocomplex is indicative of the absence of the biomarker and lack of the disease. The antigen can be selected from the group listed in Table 1 or FIG. 4, and antigenic fragments thereof.

In another embodiment, the present invention provides a method of generating a patient-specific Early-Stage PD autoantibody biomarker profile comprising obtaining an immunoglobulin-containing biological sample from a patient, performing an assay to determine the presence or absence of at least one Early-Stage PD autoantibody biomarkers in the biological sample, and generating a patient-specific Early-Stage PD autoantibody biomarker profile of the Early-Stage PD autoantibody biomarker(s) present in the sample. In another embodiment, the methods of the present claims can further be employed to monitor therapeutic outcome and the progress of a subjects undergoing PD treatment.

In one embodiment, the assay is performed to determine presence or absence of four or more Early-Stage PD autoantibody biomarkers in the biological sample. For example, the assay can be performed to determine the presence or absence of the following four Early-Stage PD autoantibody biomarkers/autoantibodies that specifically bind to Serine/threonine-protein kinase MARK1, tRNA pseudouridine synthase-like 1 (PUSL1), Interleukin-20 (IL20), and C-C motif chemokine 19 (CCL19).

In some embodiments, the immunoglobulin-containing biological sample can be serum, plasma, whole blood, CSF, saliva, or sputum.

The target antigen or an epitope thereof can be attached to a substrate. The one or more target antigens or antigenic fragments/epitopes thereof for the one or more Early-Stage PD autoantibody biomarkers can be in the form of an array, such as a microarray. In one embodiment, the microarray can include a substrate on which the target antigens listed in Table 1 or FIG. 4 or antigenic fragments/epitopes thereof are immobilized. In some embodiments, the Microarray can be prepared on a glass surfaces with a variety of coatings including but not limited to nitrocellulose, FAST™, Full-Moon™, SuperEpoxy™, SuperAldehyde™, SuperNHS™, Ni-NTA, PATH, Nextirion, Nexterion H thin film, epoxysilane or aldehydesilane or other similar coatings known to those of ordinary skill in the art. In some embodiments, the substrate can be a nitrocellulose-coated glass slide.

In some embodiments, the invention allows one to discriminate between Early-Stage PD and Mild-Moderate PD. In other embodiments, the invention allows one to discriminate between Early-Stage PD and a non-PD condition. Examples of the non-PD condition include Alzheimer's disease, multiple sclerosis, and cancer. In yet other embodiments, the presence of at least one autoantibody biomarker in a sample from a subject is capable of forming at least a part of a basis of a diagnosis of the subject as having Early-Stage PD.

In a second aspect, the invention provides a conjugate having (i) one or more antigens that are specific for one or more Early Stage PD biomarkers, and (ii) a substrate on which the one or more antigens are immobilized. Examples of the antigens include those selected from the group consisting of the target antigens listed in Table 1 and antigenic fragments thereof. For example, the substrate can have immobilized thereon a plurality of individually addressable antigens that are specific for the Early-Stage PD biomarkers respectively. The substrate can be a slide or a bead. In one embodiment, the antigens can be those selected from the group consisting of the proteins listed in FIG. 4 and antigenic fragments thereof. In another embodiment, the conjugate can further comprise the one or more Early-Stage PD biomarkers or one or more detection agents, such as a secondary antibodies and indicator reagents as described below.

In a third aspect, the invention features a microarray comprising a plurality of conjugates described above. In at least one embodiment, such microarrays may be used to identify or screen candidate therapeutic regimens and/or therapeutic agents suitable for treatment of Early-Stage or Mild and Moderate Stage PD. In at least one embodiment, agents that decrease the level of autoantibody biomarkers, inhibiting or reducing the activity of the Early-Stage PD biomarkers may be used as therapeutic agents to treat Early-Stage PD.

In a fourth aspect, the invention provides a kit comprising (i) one or more antigens that are specific for one or more Early-Stage PD biomarkers, and (ii) reagents for determining binding of the antigens to the Early-Stage PD biomarkers. The antigens can be selected from the group consisting of the proteins listed in Table 1 and antigenic fragments thereof. The one or more antigens or antigenic fragments thereof can be immobilized on a substrate.

In a fifth aspect, the invention provides a plurality of immunocomplexes, each complex comprising (i) an Early-Stage PD autoantibody biomarker, said autoantibody specifically binding to a target antigen selected from the group consisting of the proteins listed in Table 1; (ii) said antigen or an antigenic fragment thereof, and (iii) a detection agent.

In some embodiments, the assay performed to determine the presence or absence of at least one Early-Stage PD autoantibody biomarker uses at least one (1) target antigen or antigenic fragments thereof.

In some embodiments, the assay performed to determine the presence or absence of at least one Early-Stage PD autoantibody biomarker uses at least four (4) target antigens or antigenic fragments thereof.

In some embodiments, the assay performed to determine the presence or absence of at least one Early-Stage PD autoantibody biomarker uses at least five (5) target antigens or antigenic fragments thereof.

In some embodiments, the assay performed to determine the presence or absence of at least one Early-Stage PD autoantibody biomarker uses at least ten (10) target antigens or antigenic fragments thereof.

In some embodiments, the assay performed to determine the presence or absence of at least one Early-Stage PD autoantibody biomarker uses at least twenty-five (25) target antigens or antigenic fragments thereof.

In some embodiments, the assay performed to determine the presence or absence of at least one Early-Stage PD autoantibody biomarker uses at least fifty (50) target antigens or antigenic fragments thereof.

In some embodiments, the assay performed to determine the presence or absence of at least one Early-Stage PD autoantibody biomarker uses between one (1) and five (5) (inclusive) target antigens or antigenic fragments thereof.

In some embodiments, the assay performed to determine the presence or absence of at least one Early-Stage PD autoantibody biomarker uses between one (1) and ten (10) (inclusive) target antigens or antigenic fragments thereof.

In some embodiments, the assay performed to determine the presence or absence of at least one Early-Stage PD autoantibody biomarker uses between five (5) and ten (10) (inclusive) target antigens or antigenic fragments thereof.

In some embodiments, the assay performed to determine the presence or absence of at least one Early-Stage PD autoantibody biomarker uses between one (1) and twenty five (25) (inclusive) target antigens or antigenic fragments thereof.

In some embodiments, the assay performed to determine the presence or absence of at least one Early-Stage PD autoantibody biomarker uses between one (1) and twenty five (25) (inclusive) target antigens or antigenic fragments thereof.

In some embodiments, the assay performed to determine the presence or absence of at least one Early-Stage PD autoantibody biomarker uses between one (1) and fifty (50) (inclusive) target antigens or antigenic fragments thereof.

In some embodiments, the assay performed to determine the presence or absence of at least one Early-Stage PD autoantibody biomarker uses at least one target antigen or antigenic fragments thereof from Table 1.

In some embodiments, the assay performed to determine the presence or absence of at least one Early-Stage PD autoantibody biomarker uses at least four (4) target antigens from Table 1 or antigenic fragments thereof.

In some embodiments, the assay performed to determine the presence or absence of at least one Early-Stage PD autoantibody biomarker uses at least five (5) target antigens from Table 1 or antigenic fragments thereof.

In some embodiments, the assay performed to determine the presence or absence of at least one Early-Stage PD autoantibody biomarker uses at least ten (10) target antigens from Table 1 or antigenic fragments thereof.

In some embodiments, the assay performed to determine the presence or absence of at least one Early-Stage PD autoantibody biomarker uses at least twenty-five (25) target antigens from Table 1 or antigenic fragments thereof.

In some embodiments, the assay performed to determine the presence or absence of at least one Early-Stage PD autoantibody biomarker uses at least fifty (50) target antigens from Table 1 or antigenic fragments thereof.

In some embodiments, the assay performed to determine the presence or absence of at least one Early-Stage PD autoantibody biomarker uses between one (1) and five (5) (inclusive) target antigens from Table 1 or antigenic fragments thereof.

In some embodiments, the assay performed to determine the presence or absence of at least one Early-Stage PD autoantibody biomarker uses between one (1) and ten (10) (inclusive) target antigens from Table 1 or antigenic fragments thereof.

In some embodiments, the assay performed to determine the presence or absence of at least one Early-Stage PD autoantibody biomarker uses between five (5) and ten (10) (inclusive) target antigens from Table 1 or antigenic fragments thereof.

In some embodiments, the assay performed to determine the presence or absence of at least one Early-Stage PD autoantibody biomarker uses between one (1) and twenty five (25) (inclusive) target antigens from Table 1 or antigenic fragments thereof.

In some embodiments, the assay performed to determine the presence or absence of at least one Early-Stage PD autoantibody biomarker uses between ten (10) and twenty five (25) (inclusive) target antigens from Table 1 or antigenic fragments thereof.

In some embodiments, the assay performed to determine the presence or absence of at least one Early-Stage PD autoantibody biomarker uses between one (1) and fifty (50) (inclusive) target antigens from Table 1 or antigenic fragments thereof.

In another embodiment, the present invention provides a substrate on which at least one target antigen or antigenic fragment thereof that is specific for at least one Early-Stage PD autoantibody biomarker is immobilized.

In some embodiments, at least four (4) target antigens or antigenic fragments thereof are immobilized on the substrate.

In some embodiments, at least five (5) target antigens or antigenic fragments thereof are immobilized on the substrate.

In some embodiments, at least ten (10) target antigens or antigenic fragments thereof are immobilized on the substrate.

In some embodiments, at least twenty-five (25) target antigens or antigenic fragments thereof are immobilized on the substrate.

In some embodiments, at least fifty (50) target antigens or antigenic fragments thereof are immobilized on the substrate.

In some embodiments, between one (1) and five (5) (inclusive) target antigens or antigenic fragments thereof are immobilized on the substrate.

In some embodiments, between one (1) and ten (10) (inclusive) target antigens or antigenic fragments thereof are immobilized on the substrate.

In some embodiments, between five (5) and ten (10) (inclusive) target antigens or antigenic fragments thereof are immobilized on the substrate.

In some embodiments, between five (5) and twenty-five (25) (inclusive) target antigens or antigenic fragments thereof are immobilized on the substrate.

In some embodiments, between ten (10) and twenty-five (25) (inclusive) target antigens or antigenic fragments thereof are immobilized on the substrate.

In some embodiments, between one (1) and twenty-five (25) (inclusive) target antigens or antigenic fragments thereof are immobilized on the substrate.

In some embodiments, between one (1) and fifty (50) (inclusive) target antigens or antigenic fragments thereof are immobilized on the substrate.

In some embodiments, at least one target antigen or antigenic fragments thereof from Table 1 is immobilized on the substrate.

In some embodiments, at least four (4) target antigens from Table 1 or antigenic fragments thereof are immobilized on the substrate.

In some embodiments, at least five (5) target antigens from Table 1 or antigenic fragments thereof are immobilized on the substrate.

In some embodiments, at least ten (10) target antigens from Table 1 or antigenic fragments thereof are immobilized on the substrate.

In some embodiments, at least twenty-five (25) target antigens from Table 1 or antigenic fragments thereof are immobilized on the substrate.

In some embodiments, at least fifty (50) target antigens from Table 1 or antigenic fragments thereof are immobilized on the substrate.

In some embodiments, between one (1) and five (5) (inclusive) target antigens from Table 1 or antigenic fragments thereof are immobilized on the substrate.

In some embodiments, between one (1) and ten (10) (inclusive) target antigens from Table 1 or antigenic fragments thereof are immobilized on the substrate.

In some embodiments, between five (5) and ten (10) (inclusive) target antigens from Table 1 or antigenic fragments thereof are immobilized on the substrate.

In some embodiments, between five (5) and twenty-five (25) (inclusive) target antigens from Table 1 or antigenic fragments thereof are immobilized on the substrate.

In some embodiments, between ten (10) and twenty-five (25) (inclusive) target antigens from Table 1 or antigenic fragments thereof are immobilized on the substrate.

In some embodiments, between one (1) and twenty-five (25) (inclusive) target antigens from Table 1 or antigenic fragments thereof are immobilized on the substrate.

In some embodiments, between one (1) and fifty (50) (inclusive) target antigens from Table 1 or antigenic fragments thereof are immobilized on the substrate.

In a further embodiment, the present invention provides a kit for detecting Early-Stage PD autoantibody biomarkers.

In some embodiments, the kit contains at least one target antigen or antigenic fragments thereof.

In some embodiments, the kit contains at least five (5) target antigens or antigenic fragments thereof.

In some embodiments, the kit contains at least twenty-five (25) target antigens or antigenic fragments thereof.

In some embodiments, the kit contains at least fifty (50) target antigens or antigenic fragments thereof.

In some embodiments, the kit contains between one (1) and five (5) (inclusive) target antigens or antigenic fragments thereof.

In some embodiments, the kit contains between one (1) and ten (10) (inclusive) target antigens or antigenic fragments thereof.

In some embodiments, the kit contains between one (1) and twenty five (25) (inclusive) target antigens or antigenic fragments thereof.

In some embodiments, the kit contains between five (5) and ten (10) (inclusive) target antigens or antigenic fragments thereof.

In some embodiments, the kit contains between five (5) and twenty-five (25) (inclusive) target antigens or antigenic fragments thereof.

In some embodiments, the kit contains between ten (10) and twenty-five (25) (inclusive) target antigens or antigenic fragments thereof.

In some embodiments, the kit contains between one (1) and twenty-five (25) (inclusive) target antigens or antigenic fragments thereof.

In some embodiments, the kit contains at least one target antigen from Table 1 or antigenic fragments thereof.

In some embodiments, the kit contains at least four (4) target antigens from Table 1 or antigenic fragments thereof.

In some embodiments, the kit contains at least five (5) target antigens from Table 1 or antigenic fragments thereof.

In some embodiments, the kit contains at least twenty-five (25) target antigens from Table 1 or antigenic fragments thereof.

In some embodiments, the kit contains at least fifty (50) target antigens from Table 1 or antigenic fragments thereof.

In some embodiments, the kit contains between one (1) and five (5) (inclusive) target antigens from Table 1 or antigenic fragments thereof.

In some embodiments, the kit contains between one (1) and ten (10) (inclusive) target antigens from Table 1 or antigenic fragments thereof.

In some embodiments, the kit contains between five (5) and ten (10) (inclusive) target antigens from Table 1 or antigenic fragments thereof.

In some embodiments, the kit contains between five (5) and twenty-five (25) (inclusive) target antigens from Table 1 or antigenic fragments thereof.

In some embodiments, the kit contains between ten (10) and twenty-five (25) (inclusive) target antigens from Table 1 or antigenic fragments thereof.

In some embodiments, the kit contains between one (1) and twenty-five (25) (inclusive) target antigens from Table 1 or antigenic fragments thereof. In some embodiments, the present invention provides for diagnostic systems for detecting an Early-Stage PD autoantibody biomarker in a subject who has or is suffering from or is at risk of developing Parkinson's Disease, the system comprising (a) obtaining an immunoglobulin-containing biological sample from the subject, (b) conducting an immunoassay to detect at least four target antigens or antigenic fragments thereof specific for Early-Stage PD, (c) detecting the presence or absence of an immunocomplex, wherein the presence of an immunocomplex is indicative of the presence of the Early-Stage PD autoantibody biomarker in said subject and the presence of the disease and wherein the absence of an immunocomplex is indicative of the absence of the Early Stage PD autoantibody biomarkers and thus lack of the disease, (d) generating a report identifying subjects having Early Stage PD or are at the risk of developing Early Stage PD, and (e) optimizing the treatment plan in subjects in need thereof, by instituting a suitable anti Parkinson's therapeutic regimen.

In another aspect of the present invention, methods of treating patients with Early Stage PD or is at risk of developing early stage PD or are suffering from the same are described.

The details of one or more embodiments of the invention are set forth in the description below. Other features, objectives, and advantages of the invention will be apparent from the description and from the claims.

BRIEF DESCRIPTION OF THE DRAWINGS

FIG. 2b is a ROC curve diagram showing assessment of autoantibody biomarkers for monitoring PD progression and staging. Comparison of Early-Stage PD (n=103) vs. mild-moderate PD (n=29) using a panel of 50 (dark black line) or 4 (grey line) biomarkers (which are substantially overlapping) showing that autoantibody biomarkers can be used to accurately distinguish different stages of PD progression. The ROC AUC, sensitivity, and specificity values for the 50 and 4 biomarkers are shown in Table 3.

DETAILED DESCRIPTION OF THE INVENTION

Figure 1:
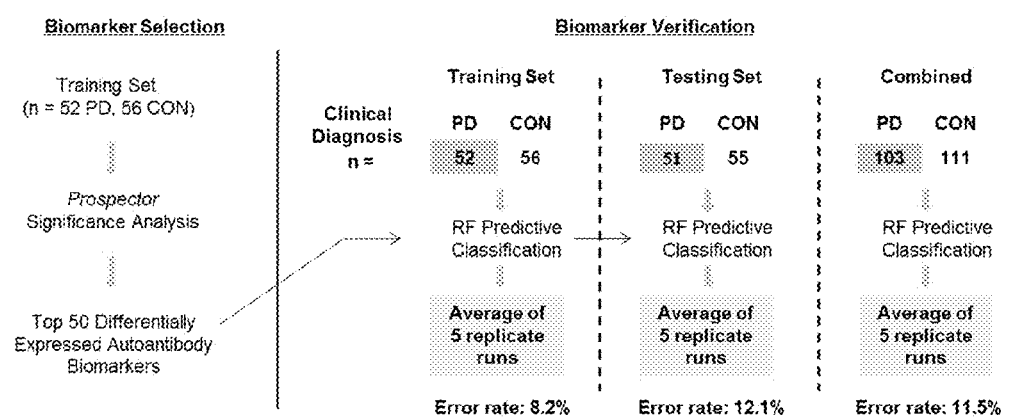
FIG. 1 is a diagram showing the biomarker selection and Training/Testing Set analysis strategy. The total sample pool (n=214) was randomly split into two groups: Training Set and Testing Set. Prospector statistical analysis was performed on the Training Set to identify the top 50 most differentially expressed autoantibody classifiers in early stage PD samples compared to controls. The diagnostic accuracy of these selected biomarkers was tested by using Random Forest to predict sample classification in the Training Set, Testing Set, and both sets combined.

This invention is based, at least in part, on unexpected discoveries that a number of panels of autoantibodies can be used for an accurate, inexpensive, and noninvasive test to detect PD in its earliest stages.

As PD begins, the area of the brain which is affected is rather localized. For example, the substantia nigra starts to deteriorate. The body's immune system quickly determines the type of tissue which is being damaged and produces autoantibodies to clear away that debris. Accordingly, this stage is the time that the autoantibodies/biomarkers disclosed in this invention are useful, and as used herein the term "Early-Stage PD" refers to this stage of PD. At this stage, a subject or patient does not show at least one, two, three, four, or all of the following typical PD symptoms: slowness of movement (bradykinesia), rigidity, resting tremor, postural instability, and response to levodopa. To that end, the subject or patient's Hoehn and Yahr scale score is no greater than 3, e.g., no greater than 2.5, 2.0, 1.5, or 1.0.

Later as the disease advances, inflammation becomes more widespread and sections of the brain which were not initially involved in the disease mechanism begin to die resulting in many different autoantibodies being present and thereby increasing the complexity of that portion of the autoantibody profile linked to the disease. The later stage autoantibody pattern might be, however, a good indicator of whether or how fast the disease is progressing.

Early-Stage PD Autoantibody Biomarkers

As used herein "Early-Stage PD autoantibody biomarkers" or "autoantibody biomarkers" refer to antibodies, including, for example, autoantibodies which specifically bind to target antigens and may serve as diagnostic indicators that can be used to differentiate Early-Stage PD from control subjects. As used herein, the term "Early-Stage PD autoantibody biomarkers" as defined herein include compositions that meet at least one of the following three criteria: i) is capable of detecting and specifically binding to at least one target antigen of the present invention; ii) is capable of serving as a diagnostic indicator of Early-Stage Parkinson's Disease, e.g. can be used to differentiate Early-Stage PD from control subjects, or iii) presence of at least one Early-Stage PD autoantibody biomarker in a subject is capable of forming at least a part of a basis of a diagnosis of the subject as having Early-Stage PD.

It has been discovered herein that neurodegenerative diseases, including Early-Stage PD, cause the production and release of cellular products as a result of cell damage related to ongoing pathology, some of which are both cell type- and organ-specific. These released cellular products (many of which are proteins), their break-down fragments and disease-related post-translational modifications enter the blood and lymph circulation, act as antigens, and elicit an immune response. This immune response leads to the production and appearance of a relatively large number of self-reactive autoantibodies in the blood.

Cells throughout the body share a vast number of proteins in common, but only a relatively small subset of autoantibodies are specifically reactive to the cells, tissues and organs involved in a particular disease. It has been discovered in accordance with the present invention that this response leads to a disease-specific autoantibody profile that is characteristic for each disease and the specific cell types involved. In addition, in individuals with concurrent diseases, it has been discovered herein that a specific pattern of autoantibodies reflects each of these concurrent, ongoing disease processes. Accordingly, the present invention relates to the specific pattern of PD biomarkers that are associated with Early-Stage PD as well as the target antigens of the autoantibody biomarkers.

Once inside the brain tissue, autoantibodies are free to bind selectively to any cells within the brain that possess and display the proper target antigens on their surfaces. If the autoantibody target is particularly abundant on a cell surface, the binding of many molecules of autoantibody can crosslink and immobilize this protein. If the target is an important receptor, the target and the cell can be rendered nonfunctional, leading to more global brain functional impairments. Thus, specific brain-reactive autoantibodies in human sera can put one at risk for specific diseases, such as Early-Stage PD. The invention described herein provides a method for the detection of these autoantibodies in human biological samples and their use as biomarkers for the detection and diagnosis of Early-Stage PD.

Thus in one embodiment, the present invention provides a method of identifying a subject who has or is at risk of developing Early-Stage PD comprising obtaining an immunoglobulin-containing biological sample from the subject, performing an assay to determine the presence or absence of one or more Early-Stage PD autoantibody biomarker in the biological sample, and identifying the subject as either with or at risk for developing Early-Stage PD if one or more of Early-Stage PD autoantibody biomarkers is present.

It was shown that blood-borne autoantibodies have potential to serve as useful biomarkers of disease (Han et al. *PloS one* 7, e32383 (2012) and Nagele et al. *PloS one* 6, e23112 (2011). These autoantibodies are abundant and ubiquitous in the blood, and are influenced by a variety of factors including age, gender, and the presence of ongoing disease (Nagele et al. *PloS one* 8, e60726 (2013), *Avrameas Immunology today* 12, 154-159 (1991), and Shoenfeld et al. *Journal of autoimmunity* 38, J71-73 (2012)). There is evidence that they function in the daily physiological clearance of cell and tissue debris from the blood; and it has been hypothesized that individual autoantibody profiles vary with the immune system's heightened response to the release of specific, pathology-associated debris (Nagele et al. *PloS one* 8, e60726 (2013), Jennette et al. *Kidney international* 78, 533-535 (2010), and Cohen Trends in immunology 34, 620-625 (2013)). In support of this, specific autoantibodies in human serum were previously identified to serve as biomarkers to diagnose mild-moderate stages of PD with an overall accuracy of 97.1%, with comparable results also obtained for mild-moderate Alzheimer's disease (AD), Han et al. *PloS one* 7, e32383 (2012) and Nagele et al. *PloS one* 6, e23112 (2011).

As disclosed herein, an autoantibody biomarker discovery strategy was used to identify autoantibody biomarker candidates useful for the detection and diagnosis of Early-Stage PD. Results confirmed that a small panel of autoantibody biomarkers detected in serum could differentiate Early-Stage PD patients from age-matched controls with an overall accuracy of 89.2%. It could also readily distinguish Early-Stage PD subjects from those with more clinically advanced, Mild-Moderate PD, as well as differentiate them from individuals afflicted with other neurodegenerative and non-neurodegenerative diseases like AD, multiple sclerosis, and breast cancer.

More specifically, sera were obtained from subjects enrolled in the DATATOP study through the Michael J. Fox Foundation and Parkinson's Study Group (DATATOP: a multicenter controlled clinical trial in early Parkinson's disease. Parkinson Study Group. *Archives of Neurology* 46, 1052-1060 (1989)). These subjects were diagnosed initially and later confirmed at follow-up with Early-Stage PD with 90% confidence. They participated in the DATATOP clinical trial aimed at testing the potential beneficial effects of two antioxidative therapies, deprenyl and tocopherol, on the progression of PD. These agents were found to have no discernable beneficial effects on PD progression. Autoantibody biomarker profiles for DATATOP subjects with Early-Stage PD were obtained and compared with age- and sex-matched controls as well as with sera from PD patients with more advanced (mild-moderate) disease.

As disclosed herein, a panel containing 50 autoantibody biomarkers was initially identified as being able to distinguish subjects with Early-Stage PD from age- and sex-matched controls. Their significance and predictive value were then verified using an independent Testing Set containing subject samples that were not involved in the biomarker discovery process. Results showed an overall accuracy for Early-Stage PD detection of 89.2%, a sensitivity of 94.2% and a specificity of 84.7%. ROC curve assessment of the utility of the diagnostic showed an AUC of 0.93 with 50 biomarkers and 0.92 with four biomarkers. Since it is generally considered desirable for a diagnostic test to have a sensitivity and specificity greater than 85% and a ROC curve AUC of 0.85, the two biomarker panels for Early- Stage PD detection described here exceed these criteria for the specific population studied (Henriksen et al. *Alzheimer's & dementia: the journal of the Alzheimer's Association* 10, 115-131 (2014). Among the 50 autoantibody biomarkers identified (Table 1), the top four represent the minimum number required for accurate detection and diagnosis of Early-Stage PD. Moreover, the same panel of four biomarkers is specific in differentiating Early-Stage PD from other neurological and non-neurological diseases, such as AD, MS, and breast cancer. Therefore, in at least some embodiments, methods of the present invention for detecting Early Stage PD follow the steps of identifying the presence of four (4) biomarkers.

Figure 3:
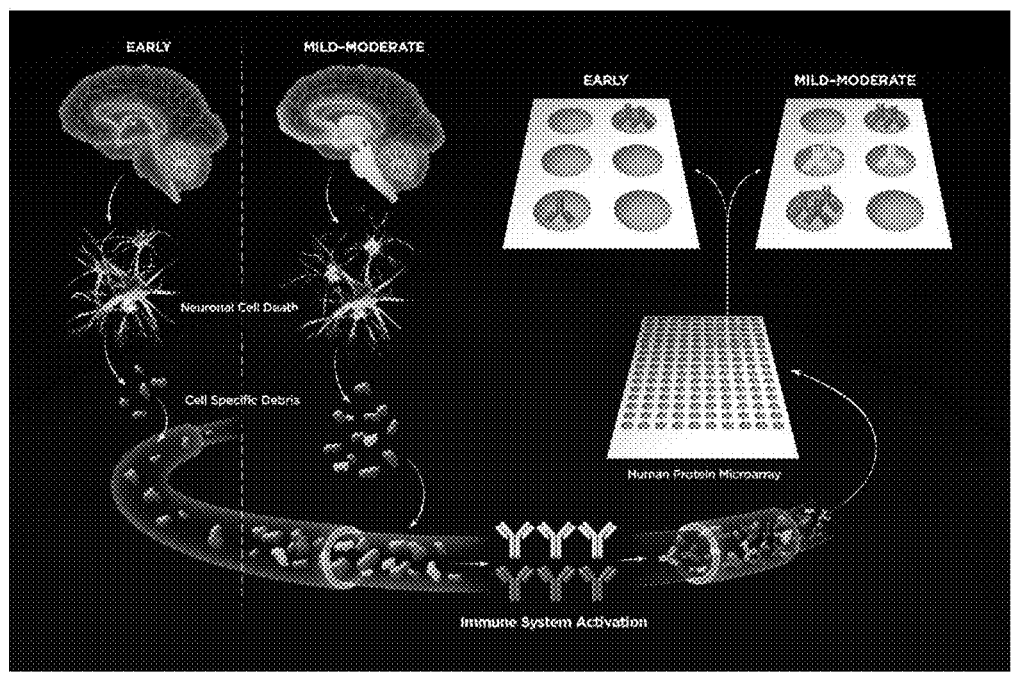
FIG. 3 is a diagram showing proposed origin of autoantibodies useful for PD diagnosis and staging. By the time symptoms emerge at Early-Stage PD, a substantial fraction of neurons in the substantia nigra (dot in brain) has already died. Cell debris (particles), subjected to variable degrees of degradation, are liberated into the surrounding brain tissue. Some debris makes its way into the blood, activates the immune system, and elicits the production of corresponding autoantibodies. In Early-Stage PD, the site of pathology and debris production is often highly localized, and the spectrum of disease-associated autoantibodies is likewise limited (dark autoantibodies). Escalation and spreading of PD pathology during later disease stages (e.g., mild-moderate PD) leads to more abundant and diverse debris and disease-associated autoantibody profiles. For each disease stage, autoantibodies exhibiting the most dramatic and consistent changes are selected as the useful biomarkers of the disease.

The two panels of 50 and four autoantibody biomarkers described here have also allowed one to distinguish Early-Stage PD from mild-moderate PD with an overall accuracy of 98.5%, a sensitivity of 94.2%, specificity of 84.7%, and a ROC curve AUC of 0.98 for the 50 biomarkers and 0.99 for the four biomarkers. A diagnostic test that can properly distinguish different stages of PD severity will make it possible to follow a patient's disease course, rate of progression, and response to therapies. This exciting capability is useful for physicians and their patients as well as for early enrollment of subjects into clinical trials and monitoring therapeutic efficacy through a patient's response to new drugs. Of course, for the latter, a positive patient response would be a delay in a patient's progression to the next disease stage or an improvement from the current disease state as evidenced by curtailed symptoms. Any slowing or stopping of disease progression resulting from diminished pathology would be expected to be accompanied by reduced debris production as well as a corresponding reduction in levels of disease-associated autoantibodies (FIG. 3).

It is widely recognized that the pathogenesis of a number of neurodegenerative diseases is initiated many years prior to the emergence of clinically useful symptoms. For effective and accurate identification of biomarkers directly linked to pathology, the selection of truly pathology-free controls is just as important as the selection of subjects with confirmed pathology. However, without the aid of telltale symptoms during prodromal phases of disease, it is difficult to ensure that age-matched controls being used for biomarker discovery are truly pathology-free. This may be especially problematic for diseases like AD where, due to a combination of high prevalence and a long prodromal period, a large fraction of individuals are likely to have pre-symptomatic pathology. This is much less of a problem with PD because of the relatively low prevalence of PD within the elderly population. Nevertheless, the difficulty of obtaining pathology-free controls would be expected to hinder biomarker discovery efforts as well as the possibility of achieving pre-symptomatic disease detection.

To investigate strategies that may aid in compensating for this inherent study limitation, the effects of purposely adding a subset of younger controls to the control subject pool were tested on diagnostic accuracy. It was predicted that adding truly pathology-free controls (albeit younger and non-age-matched) to the control subject group should improve diagnostic outcome by emphasizing the non-pathology features of autoantibody profiles common to both groups. For a disease with a relatively low prevalence, such as PD, it was speculated that the number of compensatory younger controls added should be relatively low—in this case perhaps no more than 5% of the total controls population. However, for diseases with a much higher prevalence and longer prodromal period, such as AD, the percentage of compensatory younger controls added should be higher.

As disclosed here, panels of autoantibody biomarkers can accurately differentiate Early-Stage PD subjects from age-matched controls using a minute volume of serum and human protein microarrays. Furthermore, they can distinguish Early-Stage PD subjects from those with more advanced disease as well as differentiate them from other neurodegenerative and non-neurodegenerative diseases with high accuracy. The development of a sensitive and specific, blood-based diagnostic test for Early-Stage PD could have a profound clinical impact on the early treatment of PD patients who currently rely on symptoms alone for diagnosis. The use of these autoantibody biomarkers would fundamentally change the way PD progression is monitored in trials of potential therapies. Accordingly, autoantibodies described herein can serve as dynamic and accurate diagnostic biomarkers of PD. Moreover, due to their proposed function in disease-specific debris clearance, the autoantibodies may serve as useful biomarkers for many diseases.

In another embodiment, the present invention provides a method for diagnosing Early-Stage PD in a subject in need of such diagnosis comprising obtaining an immunoglobulin-containing biological sample from the subject, performing an assay to determine the presence or absence of at least one autoantibody biomarker in the biological sample, and diagnosing Early-Stage PD if at least one Early-Stage PD autoantibody biomarker is present.

Another embodiment of this invention provides a method for detecting Early-Stage PD autoantibody biomarkers in a subject comprising obtaining an immunoglobulin-containing biological sample from the subject, and performing an assay to determine the presence or absence of one or more Early-Stage PD autoantibody biomarkers in the biological sample.

In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. To obtain serum from blood, a sample of blood is received and centrifuged at a speed sufficient to pellet all cells and platelets, and the serum to be analyzed is drawn from the resulting supernatant. Sputum and saliva samples may be collected by methods known in the art. The biological samples may be diluted with a suitable buffer.

In a preferred embodiment of the invention, the assay used to determine the presence or absence of one or more Early-Stage PD autoantibody biomarkers in the biological sample is performed by contacting the biological sample with one or more target antigens that are specific for at least one Early-Stage PD autoantibody biomarker under conditions that allow an immunocomplex of the target antigen and the autoantibody biomarker to form, and detecting the presence of the immunocomplex.

Early-Stage PD autoantibody biomarkers may be identified by comparing the autoantibodies present in an immunoglobulin-containing sample from a subject having a neurodegenerative disease with autoantibodies present in an immunoglobulin-containing sample from an age-matched AD-free control subject. The target antigens for the autoantibody biomarkers present in the sample from the subject having Early-Stage PD but not present in the sample from the control subject provide the identification of Early-Stage PD autoantibody biomarkers. The sample is preferably serum or plasma.

In a preferred embodiment of the invention, the subject is a human.

Target Antigens

The term "target antigens" or just "antigens" as used herein includes protein and peptide antigens. In one embodiment, target antigens that have been identified as capable of being specifically bound by the Early-Stage PD autoantibody biomarkers are set forth in Table 1 below. Antigenic fragments of those target antigens disclosed in Table 1 are expressly considered covered by the present invention, so long as the autoantibody biomarkers of the present invention are capable of binding to the antigenic fragments thereof. Target antigens may comprise a protein antigen or antigenic fragments thereof, a polypeptide or peptide fragment thereof containing one or more epitopes recognized by the autoantibody biomarkers, or an epitope peptidomimetic that is recognized by the autoantibody biomarkers. The target antigens may be purified from natural sources, or produced recombinantly or synthetically by methods known in the art, and may be in the form of fusion proteins. The target antigens may be produced in vitro using cell-free translation systems. In one preferred embodiment, the target antigens are produced in a mammalian, insect or bacterial expression system to ensure correct folding and function. All of these methods may be automated for high throughput production.

The target antigens in Table 1 are identified by art-accepted names as well as database identification numbers. The database identification numbers refer to the publically available protein databases, for example, the National Center for Biotechnology Information (NCBI), which are well-known and accessible to those of ordinary skill in the art. One of ordinary skill in the art will realize that by being given a database identification number corresponding to a nucleotide sequence, one may also find the corresponding publicly available amino acid/polypeptide sequence of the target antigen from that source. Thus, one of ordinary skill in the art will realize that if provided a database identification number, such as, for example, a GenBank No. or Accession No. corresponding to a nucleotide sequence, such as, but not limited to a cDNA clone or mRNA sequence that codes for a target antigen of the present invention, that one may find the target antigens of the present invention from the GenBank No. or Accession No. corresponding to said nucleotide sequence. Or, alternatively, one may simply transcribe (if DNA including cDNA) and translate (RNA) to provide a polypeptide corresponding to the target antigens of the present invention.

Suitable methods for external production and purification of target antigens to be spotted on arrays disclosed herein include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

One having ordinary skill in the art will understand that modifications, including substitutions, including but not limited to conservative substitutions, additions, and deletions may be made to the amino acid/polypeptide sequences of the target antigens of the present invention, and that the substituted target antigens would still be covered by the present invention, so long as the autoantibody biomarkers may still bind to the target antigens or antigenic fragments thereof. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the target antigens the present invention can be replaced with other amino acid residues from the same side chain family and the altered target antigen can retain functional activity as described herein.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods. Specific examples include the following. The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic*

Acids Res. 25(17):3389-3402. When utilizing BLAST and Gapped BLAST programs, the default parameters of the respective programs (e.g., XBLAST and NBLAST) can be used.

One having ordinary skill in the art will understand that post-translational modifications may be made to the amino acid/polypeptide sequences of the target antigens of the present invention, and such modified target antigens would still be covered by the present invention, so long as the autoantibody biomarkers may still bind to the target antigens or antigenic fragments thereof.

One of ordinary skill in the art will understand that the target antigens include, but are not limited to, gene products, synthetic polypeptides, recombinant polypeptides, fragments of polypeptides, and analogs, orthologs, paralogs, or homologs of gene products, synthetic polypeptides, so long as the autoantibody biomarkers may still bind to the target antigens or antigenic fragments thereof.

One having ordinary skill in the art will understand that the target antigens may be chemically modified, such as but not limited to, e.g. modifications made to individual amino acid residues, PEG-ylation, addition of sequence tags, reporter molecules, so long as the autoantibody biomarkers may still bind to the target antigens.

So long as the autoantibody biomarkers may still bind to the target antigens or antigenic fragments thereof, any modification made to the target antigens or antigenic fragments thereof is considered to be covered by this invention. The preferred antigenic fragments of the present invention are at least 85%, 90%, 95% or 98% homologous to the antigenic structures of the antigens of Table I and bind with disease related autoantibody biomarkers or have the same immunoreactivity characteristics as the target antigens of Table 1.

TABLE 1

Target Antigens

| Database ID | Protein Name | Proposed Function |
|---|---|---|
| NP_061120.3 | Serine/threonine-protein kinase MARK1 | Regulator of neuronal migration |
| NM_153339.1 | PUSL1 (tRNA pseudouridine synthase-like 1) | Regulator of tRNA processing |
| AF402002.1 | Interleukin-20 (IL20) | Proinflammatory and angiogenic cytokine |
| Q99731.1 | C-C motif chemokine 19 (CCL19) | Mediator of inflammatory and immunological responses |
| BC033758.1 | ADAP2 (Arf-GAP with dual PH domain-containing protein 2) | GTPase regulator |
| BC006105.1 | ATAT1 (Alpha-tubulin N-acetyltransferase 1) | Regulator of microtubule dynamics |
| NM_012241.2 | SIRT5 (NAD-dependent protein deacylase sirtuin-5, mitochondrial) | NAD-dependent lysine demalonylase and desuccinylase |
| BC059947.1 | CSAG1 (Putative chondrosarcoma-associated gene 1 protein) | Possible tumor antigen |
| XP_015296543.1 | Serine/threonine-protein kinase BRSK1 | Regulator of neuron migration and polarization |
| BC103660.1 | cDNA clone BC103660 | Unknown |
| Q96L34 | MAP/microtubule affinity-regulating kinase 4 | Implicated in nervous system development and cytoskeletal organization |
| BC002493.1 | TCF19 (Transcription factor 19) | Cell cycle regulator |
| NM_201403.1 | MOB3C (MOB kinase activator 3C) | Kinase regulator |
| NM_005030.2 | PLK1 (Serine/threonine-protein kinase PLK1) | Cell cycle regulator |
| BC051000.1 | TCL1B (T-cell leukemia/lymphoma protein 1B) | Protooncogene |
| NM_177524.1 | MEST (Mesoderm-specific transcript homolog protein) | Member of the alpha/beta hydrolyse superfamily |
| NM_152260.1 | RPUSD2 (RNA pseudouridylate synthase domain-containing protein 2) | Involved in pseudouridine synthesis |
| XM_373800.2 | PREDICTED: *Homo sapiens* hypothetical LOC388528 | Unknown |
| NM_080659.1 | C11orf52 (Uncharacterized protein C11orf52) | Unknown |
| BC036056.1 | FANCM (Fanconi anemia group M protein) | Involved in DNA repair |
| NM_024041.1 | *Macaca fascicularis* brain cDNA clone: QorA-12280 | Unknown |
| NM_018039.2 | KDM4D (Lysine-specific demethylase 4D) | Histone demethylase |
| NM_005205.2 | COX6A2 (Cytochrome c oxidase subunit 6A2, mitochondrial) | Member of the cytochrome C oxidase subunit 6A superfamily |
| NM_005469.2 | Acyl-coenzyme A thioesterase 8 | Acyl-CoA thioesterase |
| NM_180699.1 | SNRNP35 (U11/U12 small nuclear ribonucleoprotein 35 kDa protein) | Component of the U11/U12 snRNPs that are part of the U12-type spliceosome |
| NM_001697.1 | ATP5O (ATP synthase subunit O, mitochondrial) | Mitochondrial membrane ATP synthase |
| NM_001545.1 | ICT1 (Peptidyl-tRNA hydrolase ICT1, mitochondrial) | Peptidyl-tRNA hydrolase component of the mitochondrial large ribosomal subunit |
| NM_173578.1 | Human cDNA ORF Clone (C11orf72) | Unknown |
| XM_086879.4 | PREDICTED: Home sapiens hypothetical LOC150371 | Unknown |
| NM_017692.1 | *Macaca fascicularis* brain cDNA clone: QorA-10370 | Unknown |
| BC000190.1 | ZC3HC1 | Unknown |
| BC096708.1 | WT1-AS (Putative Wilms tumor upstream neighbor 1 gene protein) | Unknown |

TABLE 1-continued

Target Antigens

| Database ID | Protein Name | Proposed Function |
|---|---|---|
| NM_022551.2 | RPS18 (40S ribosomal protein S18) | Component os 40S ribosomal subunit |
| XM_379114.1 | PREDICTED: Homo sapiens hypothetical protein LOC150577 (LOC150577) | Unknown |
| NM_016360.1 | TACO1 (Translational activator of cyctochrome c oxidase 1) | Translational regulator |
| BC011924.1 | UNKL (Putative E3 ubiquitin-protein ligase UNKL) | Involved in ubiquitination of itself and other substrates |
| NM_003910.2 | BUD31 (Protein BUD31 homolog) | Transcriptional regulator |
| BC033230.1 | ZNF808 (Zinc finger protein 808) | Transcriptional regulator |
| XM_378879.2 | PREDICTED: Homo sapiens hypothetical LOC400763. (LOC400763) | Unknown |
| BC014452.1 | HCG1986256 | Unknown |
| XM_378350.2 | PREDICTED: Homo sapiens hypothetical LOC400027 | Unknown |
| NM_002147.2 | Homo sapiens homeobox B5 (HOXB5) | Transcription factor |
| BC009894.2 | PAPSS2 (Bifunctional 3'-phosphoadenosine 5'-phosphosulfate synthase 2) | Regulator of the sulfate activation pathway |
| NM_016101.3 | NIP7 (60S ribosome subunit biogenesis protein NIP7 homolog) | Involved in pre-rRNA processing and 60S ribosome subunit assembly |
| NM_002927.3 | RGS13 (Regulator of G-protein signaling 13) | GTPase regulator |
| NM_001008572.1 | Probable tubulin polyglutamylase TTLL1 | Catalytic subunit of the neuronal tubulin polyglutamylase complex |
| XM_085833.5 | PREDICTED: Homo sapiens hypothetical LOC147646 | Unknown |
| NM_014763.2 | MRPL19 (39S ribosomal protein L19, mitochondrial) | Structural component of mammalian mitochonridal ribosome |
| NM_003668.2 | MAPKAPK5 (MAP kinase-activated protein kinase 5) | Tumor suppressor involved in post-transcriptional regulation |
| NM_001002269.1 | EXOSC3 (Exosome complex component RRP40) | Involved in RNA processing and degradation |

Specific Target Antigens

Specific target antigens of the present invention that may be of interest include, but are expressly not limited to, the following target antigens. These antigens are meant to be exemplary to assist one of ordinary skill in the art and are explicitly non-exclusive embodiments of the invention. One of ordinary skill in the art will realize that in relation to the sequence data presented below, substitutions, modifications, additions, and deletions may be made while retaining the functional characteristic of the target antigens, namely that the autoantibody biomarkers of the present invention remain capable of binding to the target antigens. This expressly includes, but is not limited to, any of the antigenic fragments disclosed below, so long as the autoantibody biomarkers of the present invention are capable of binding to the antigenic fragments.

A. Serine/Threonine-Protein Kinase MARK1

Target antigen serine/threonine-protein kinase MARK1, also known as MAP/microtubule affinity-regulating kinase 1, is a serine/threonine kinase which is involved in cytoskeletal organization and biogenesis. Target antigen serine/threonine-protein kinase MARK1 is known to have the following antigenic fragments, all of which are considered to be covered by this present invention as potential target antigens. AA residues 59 to 311, "catalytic domain"; 331 to 371 "UBA domain"; 697 to 794 "C-terminal, kinase associated domain 1, a phospholipid binding domain."

A nucleotide sequence coding for the target antigen MARK1 is reproduced below:

(SEQ ID NO: 1)
Accession No. NM_001286124.1,
GCTGCTCCGCGCGCAGCCGGCTCGGGCCGCTCCTCCTGACTGAGGCGCGG -continued

CGGCGGCGGTGGCTGTGACCGCGCGGACCGAGCCGAGACATTCGCGCCGG

GGGATCGGGCGCCGCCGCCGCTGGGCCCCGGGCGCGTGGATGCGGCTGGG

TCGGGCGGCGCCGTACACCTGAGGCGGAGAACGGGGCGCGGCGCGGGTGA

CGCTGTCAGGGCCGCGGTTCCTGACGCCCAGGCGCTCGCCAGGACGAGCC

AGGCAGTGATTTGAGGCACCGGCTTCACCTTCACCCATGGTCCGGAGAGC

CTAGCGGGGCTCGCCACCGCCTCCCGGCTCCCCTTCCACGCCTCATCCTG

CCAGCCTCGCCGCCCCGCCAGCGCCGGGCAACCGCCTCGCCCGAAGCCCT

CCCTCGTTACTGTCCGCATACCCCGGCGGCGCCGCCGCGGGAAGCGGCTC

CCCCTCCTCTTCCTCCGCGTCCTCTTCCCTCTTTCCCCCGCCGGGGCCGC

TTGTTGCACCGCCCCGCGGCCTGCGGGAGCCGCTCGCCCCGGCCTTGTGC

TCGCGTCCGCACCCCTTTCCTGTCGCCCCCGGGGCCCGCACCACAGCCC

GGCCGGCGAGACCCCGGCCAGACCCCGCTGCCCGCACAAAATGTCGGCCC

GGACGCCATTGCCGACGGTGAACGAGCGGGACACGGAAAATCATACATCT

GTGGATGGATATACTGAACCACACATCCAGCCTACCAAGTCGAGTAGCAG

ACAGAACATCCCCCGGTGTAGAAACTCCATTACGTCAGCAACAGATGAAC

AGCCTCACATTGGAAATTACCGTTTACAAAAAACAATAGGGAAGGGAAAT

TTTGCCAAAGTCAAATTGGCAAGACACGTTCTAACTGGTAGAGAGGTTGC

TGTGAAAATAATAGACAAAACTCAGCTAAATCCTACCAGTCTACAAAAGT

TATTTCGAGAAGTACGAATAATGAAGATACTGAATCATCCTAATATAGTA

AAATTGTTTGAAGTTATTGAAACAGAGAAGACTCTCTATTTAGTCATGGA

-continued

ATACGCGAGTGGGGGTGAAGTATTTGATTACTTAGTTGCCCATGGAAGAA
TGAAAGAGAAAGAGGCCCGTGCAAAATTTAGGCAGATTGTATCTGCTGTA
CAGTATTGTCATCAAAAGTACATTGTTCACCGTGATCTTAAGGCTGAAAA
CCTTCTCCTTGATGGTGATATGAATATTAAAATTGCTGACTTTGGTTTTA
GTAATGAATTTACAGTTGGGAACAAATTGGACACATTTTGTGGAAGCCCA
CCCTATGCTGCTCCCGAGCTTTTCCAAGGAAAGAAGTATGATGGGCCTGA
AGTGGATGTGTGGAGTCTGGGCGTCATTCTCTATACATTAGTCAGTGGCT
CCTTGCCTTTCGATGGCCAGAATTTAAAGGAACTGCGAGAGCGAGTTTTA
CGAGGGAAGTACCGTATTCCCTTCTATATGTCCACAGACTGTGAAAATCT
TCTGAAGAAATTATTAGTCCTGAATCCAATAAAGAGAGGCAGCTTGGAAC
AAATAATGAAAGATCGATGGATGAATGTTGGTCATGAAGAGGAAGAACTA
AAGCCATATACTGAGCCTGATCCGGATTTCAATGACACAAAAAGAATAGA
CATTATGGTCACCATGGGCTTTGCACGAGATGAAATAAATGATGCCTTAA
TAAATCAGAAGTATGATGAAGTTATGGCTACTTATATTCTTCTAGGTAGA
AAACCACCTGAATTTGAAGGTGGTGAATCGTTATCCAGTGGAAACTTGTG
TCAGAGGTCCCGGCCCAGTAGTGACTTAAACAACAGCACTCTTCAGTCCC
CTGCTCACCTGAAGGTCCAGAGAAGTATCTCAGCAAATCAGAAGCAGCGG
CGTTTCAGTGATCATGCTGGTCCATCCATTCCTCCTGCTGTATCATATAC
CAAAAGACCTCAGGCTAACAGTGTGGAAAGTGAACAGAAAGAGGAGTGGG
ACAAAGATGTGGCTCGAAAACTTGGCAGCACAACAGTTGGATCAAAAAGC
GAGATGACTGCAAGCCCTCTTGTAGGGCCAGAGAGGAAAAAATCTTCAAC
TATTCCAAGTAACAATGTGTATTCTGGAGGTAGCATGGCAAGAAGGAATA
CATATGTCTGTGAAAGGACCACAGATCGATACGTAGCATTGCAGAATGGA
AAAGACAGCAGCCTTACGGAGATGTCTGTGAGTAGCATATCTTCTGCAGG
CTCTTCTGTGGCCTCTGCTGTCCCCTCAGCACGACCCCGCCACCAGAAGT
CCATGTCCACTTCTGGTCATCCTATTAAAGTCACACTGCCAACCATTAAA
GACGGCTCTGAAGCTTACCGGCCTGGTACAACCCAGAGAGTGCCTGCTGC
TTCCCCATCTGCTCACAGTATTAGTACTGCGACTCCAGACCGGACCCGTT
TTCCCCGAGGGAGCTCAAGCCGAAGCACTTTCCATGGTGAACAGCTCCGG
GAGCGACGCAGCGTTGCTTATAATGGGCCACCTGCTTCACCATCCCATGA
AACGGGTGCATTTGCACATGCCAGAAGGGGAACGTCAACTGGTATAATAA
GCAAAATCACATCCAAATTTGTTCGCAGGGATCCAAGTGAAGGCGAAGCC
AGTGGCAGAACCGACACCTCAAGAAGTACATCAGGGGAACCAAAAGAAAG
AGACAAGGAAGAGGGTAAAGATTCTAAGCCGCGTTCTTTGCGGTTCACAT
GGAGTATGAAGACCACTAGTTCAATGGACCCTAATGACATGATGAGAGAA
ATCCGAAAAGTGTTAGATGCAAATAACTGTGATTATGAGCAAAAAGAGAG
ATTTTTGCTTTTCTGTGTCCATGGAGACGCTAGACAGGATAGCCTCGTGC
AGTGGGAGATGGAAGTCTGCAAGTTGCCACGACTGTCACTTAATGGGGTT
CGCTTCAAGCGAATATCTGGGACATCTATTGCCTTTAAGAACATTGCATC
AAAAATAGCAAATGAGCTTAAGCTGTAAAGAAGTCCAAATTTACAGGTTC

-continued

AGGGAAGATACATACATATATGAGGTACAGTTTTTGAATGTACTGGTAAT
GCCTAATGTGGTCTGCCTGTGAATCTCCCCATGTAGAATTTGCCCTTAAT
GCAATAAGGTTATACATAGTTATGAACTGTAAAATTAAAGTCAGTATGAA
CTATAATAAATATCTGTAGCTTAAAAAGTAGGTTCACATGTACAGGTAAG
TATATTGTGTATTTCTGTTCATTTTCTGTTCATAGAGTTGTATAATAAAA
CATGATTGCTTAAAAACTTGTATAGTTGTCTAGATTTCTGCACCTGAATG
TATGTTTGATGCTTTGATTTGAAAATGTTCTTCCCTGTTATTTACATTCT
GGTGGGTTTTAAAATTCTTACCTCCATCATGCAATTTTGAAAATTGTGT
CCAGAATTAAAAGTGCATAGAAATAGCCTTTACAATTGTAGCATGGACCT
TTAAAAATTGTTTTAAAATCTTATTTAAATTTAAACCAGAAGCTGAAAAA
TAGATCAGCTTTATTATACACAAAATTATTACTGCTTATCTTTGCTCTTT
TCCTTGTTATCCCGCAAGGTTTAGTTGAGAAGATACAAAATGTTTACAGT
GTTGGCACTTAGAGTTTTTAAATTCAAGTACATGAAATTCAGTAATAGCA
TTGCCTTGAGCTAACTAGGAAGTACCGGGAAAAAAGTTAAATCTACATCA
AGTTTCTTTTGAACTTTGAAGTGTTTTCTGACCCACTGCTAACTGTAGCA
ACAAAATTTAAAAGAAAAAAAACATACTTTATCTGGCTATTATAACATAA
ACTGTCACGTAGGTTTGCTGCCTTCGAATACCGCAATTTAATTGCGGGA
ATATAATAATATTGGGACTGTTTCACAGCACAAACTCATCTTTACAGTGT
TGATCAATGCATCAGTTAAGAAATAATGCCACCTCAGGAATTAACTGGCA
TTGGGAACATTTGCCTCATTCTCCTGCTATCCTCTTCATTCACCCCTGCC
ACTGTAATATCTATAAGTACTTAAGAGACTTGTGAGCAAAACATACTATT
TATAACAGTATATGATTGATTTATGCTTATGTGGTTGTTCAGTTTGTTCC
CATGTAACTCGTTTGTTTTAAATATTTTGCCAGATTTCTTGTATTTATTC
CACATCATTATGCCTATAATGTGCCGCTTTGTGATTGGGCATTTGCCTAC
TTTTCTTTCATAATTAGTGATATATGCGATGTAAAACCACTAGTAAAGGT
ACATTTTAATACTTGTTATTTTATACTGAATTAGCCTTGGAGGTTGACTG
TGCAATGTTATTTACTGTTGTAATTACTGTAATACCAACATATGGGCCCC
ATCTGCACACTCCTGAAAAACAGAAAGTGTATTCAAATTTTATCAGTTTA
AAGAAAATAAAGCTGTGATAAATACTGTAATTCCAACCTACATTAGAAGG
TCTAAGTGTAGGTGATGTGCCATTCCATAATGGCTTCCAGACTAGGGTGA
ATTTTATGTTCTGTACTGTACTGTGATGTAGCTTTCTTCTGTAACAGTTA
TGTTTTAAAATTAAGTGAGTTTTTTTTTGCCTTAGCAAAGGGTGGTGTT
TGAAAAAAAAATGTGTAGCCCCTTTTTAACCTAGTGTTCATTCAAAAAA
AAATTGATGCAAATCTTTATTCACTTTCACTGGTGCACACTGAAATTTTA
CTTGAACAGTTCTCATAATAAAGCACTTGTCTTTTGCTCTTTATCAGAAT
GTGAATTACCTGTTTTCTGGTACAAAAGTATTCTGTATGAGGAGTTTATT
GTATGTGTTCTAAATTTAGTTGGCAAAGGGTGAAGCTGTGAAGGTTTTCA
AGATTATTGAAACTATGAAGGTTTCTTGTCATTATGACAAGAAAGTTTAA
TCTTTTTATAGGAATTCCTGTCACTGAAATACGTTTTTAAAAAAATAGAC
TCATGTGTTTTCCACGGTAGAAACTGATATTTTTTACATTTTCTCACTG
TGGCCAACTCTTCTGTGTTTGTAGAAAGGAATTTGACTTCAATATCTTTT

```
ATGAACTAAAAATGAAATCTTGATACTCACTTTAGATTTTTCATTTTATG

TGTTCATGACAACATAAATATTTTTCAAAGATTTAGAGGAATTTTGCAAT

GTGTTTGCATAAATAAATACCAGTTTATGTTCACCGGCTATGTGATACCA

GGATTTCCTTGGCTTCTGTTGAAATATTATTTGATATGACATCCCTTATA

TTAAATTAATTATTTTGTAAAAAAAAAAAAAAAAAA
```

An amino acid sequence for target antigen MARK1 is reproduced below:

```
                                              (SEQ ID NO: 2)
Accession No. NP_061120.3,
MSARTPLPTVNERDTENHTSVDGYTEPHIQPTKSSSRQNIPRCRNSITSA

TDEQPHIGNYRLQKTIGKGNFAKVKLARHVLTGREVAVKIIDKTQLNPTS

LQKLFREVRIMKILNHPNIVKLFEVIETEKTLYLVMEYASGGEVFDYLVA

HGRMKEKEARAKFRQIVSAVQYCHQKYIVHRDLKAENLLLDGDMNIKIAD

FGFSNEFTVGNKLDTFCGSPPYAAPELFQGKKYDGPEVDVWSLGVILYTL

VSGSLPFDGQNLKELRERVLRGKYRIPFYMSTDCENLLKKLLVLNPIKRG

SLEQIMKDRWMNVGHEEEELKPYTEPDPDFNDTKRIDIMVTMGFARDEIN

DALINQKYDEVMATYILLGRKPPEFEGGESLSSGNLCQRSRPSSDLNNST

LQSPAHLKVQRSISANQKQRRFSDHAGPSIPPAVSYTKRPQANSVESEQK

EEWDKDVARKLGSTTVGSKSEMTASPLVGPERKKSSTIPSNNVYSGGSMA

RRNTYVCERTTDRYVALQNGKDSSLTEMSVSSISSAGSSVASAVPSARPR

HQKSMSTSGHPIKVTLPTIKDGSEAYRPGTTQRVPAASPSAHSISTATPD

RTRFPRGSSSRSTFHGEQLRERRSVAYNGPPASPSHETGAFAHARRGTST

GIISKITSKFVRRDPSEGEASGRTDTSRSTSGEPKERDKEEGKDSKPRSL

RFTWSMKTTSSMDPNDMMREIRKVLDANNCDYEQKERFLLFCVHGDARQD

SLVQWEMEVCKLPRLSLNGVRFKRISGTSIAFKNIASKIANELKL
```

B. tRNA Pseudouridine Synthase-Like 1 (PUSL1)

A nucleotide sequence coding for target antigen PUSL1 is reproduced below:

```
                                              (SEQ ID NO: 3)
Accession No. NM_153339.1,
CGCCTCTGACGCCACCGGCTGGGCTCCGCCATGAGTTCGGCGCCGGCCTC

AGGCTCCGTGCGCGCGCGCTATCTTGTGTACTTCCAGTACGTGGGCACCG

ACTTTAACGGGGTCGCGGCCGTCAGGGGCACTCAGCGCGCCGTCGGGGTC

CAGAACTACCTGGAGGAGGCCGCCGAGCGGCTGAATTCCGTGGAGCCGGT

CAGGTTCACCATCTCCAGCCGCACGGACGCCGGGGTCCACGCCCTGAGCA

ACGCGGCGCACCTGGACGTCCAGCGCCGCTCAGGCCGGCCGCCCTTCCCG

CCCGAGGTCCTGGCCGAGGCCCTCAACACACACCTGCGGCACCCGGCCAT

CAGGGTCCTGCGGGCCTTCCGAGTGCCCAGCGACTTCCACGCTCGTCACG

CAGCCACGTCCCGGACCTACCTGTACCGCCTGGCCACTGGCTGTCACCGG

CGTGATGAGCTGCCGGTGTTTGAACGCAACCTATGCTGGACTCTCCCGGC

AGACTGCCTGGATATGGTCGCCATGCAGGAAGCCGCCCAGCACCTCCTCG

GCACACACGACTTCAGCGCCTTCCAGTCCGCTGGCAGCCCGGTGCCGAGC

CCCGTGCGAACGCTGCGCCGGGTCTCCGTTTCCCCAGGCCAAGCCAGCCC

CTTGGTCACCCCCGAGGAGAGCAGGAAGCTGCGGTTCTGGAACCTGGAGT

TTGAGAGCCAGTCTTTCCTGTATAGACAGGTACGGAGGATGACGGCTGTG

CTGGTGGCCGTGGGGCTGGGGGCTTTGGCACCTGCCCAGGTGAAGACGAT

TCTGGAGAGCCAAGATCCCCTGGGCAAGCACCAGACACGTGTAGCCCCAG

CCCACGGCTTATTCCTCAAGTCAGTGCTGTACGGGAACCTCGGTGCTGCC

TCCTGCACCCTGCAGGGGCCACAGTTCGGGAGCCACGGATGACCCTGGAC

ACTCAAGCCAAAGTTAGGCCACACCAGGCCCAACCCTGTGCTGGTCAAGC

CAGGGCAGTCACAGCTGCTTGGGGCCCACAGCACTGCTGCCTGGTCTCCA

CAGTAGCCTCCCTGCCCGGGTCCCAGCACCCTGGATGCCCGTCTCTGTCC

CAGGCGGGATGGGGCACAGTGCAGGACACAGCCATGTACACCAAGAAGAG

AGTACCAAGTAGTCTTTTGTTCAGCTTTTACTGGAAACTGCTGTCTAGGA

CCACCTGCCCTAACCAGGAATAAAGGCAAGACAGCCTGGAAAAAAAAAAA

AAAAAAAAAAAA
```

An amino acid sequence for target antigen PUSL1 is reproduced below:

```
                                              (SEQ ID NO: 4)
Accession No. NP_699170.1,
MSSAPASGSVRARYLVYFQYVGTDFNGVAAVRGTQRAVGVQNYLEEAAER

LNSVEPVRFTISSRTDAGVHALSNAAHLDVQRRSGRPPFPPEVLAEALNT

HLRHPAIRVLRAFRVPSDFHARHAATSRTYLYRLATGCHRRDELPVFERN

LCWTLPADCLDMVAMQEAAQHLLGTHDFSAFQSAGSPVPSPVRTLRRVSV

SPGQASPLVTPEESRKLRFWNLEFESQSFLYRQVRRMTAVLVAVGLGALA

PAQVKTILESQDPLGKHQTRVAPAHGLFLKSVLYGNLGAASCTLQGPQFG

SHG
```

C. Interleukin-20 (IL20)

Target antigen Interleukin-20, also known IL-20, is a cytokine structurally related to interleukin 10 (IL-10). IL-20 has been shown to transduce its signal through signal transducer and activator of transcription.

A nucleotide sequence coding for target antigen IL-20 is reproduced below:

```
                                              (SEQ ID NO: 5)
Accession No. AF402002.1,
TAAATAATGGGAAGCCTTTCAACTTGAAACAGGCTCCTAGGAGACCAGAA

GCAGCAGCCTTTCCTGAGCTCAGGTAAGAGATCTTACCCTCTACTGACAC

TGCTCACGTTGTTGTGAGGATCACCTACTTCTCCTAATCATTTACCCAGG

TATGTTCAAGGTCACATCTAAAGGACCCTTTTCCACGAGGACAAAATCTC

TTTGAGGACAAATAATCATCATGTTTATCTTTGTACTTCAGTACCTAGCA

CAACATTCAAGACAGCGGGTGCTCATTAAATGCTCATCAAATTGTTAGTT

CAGGACAACTAACATCAATCTACTTAAAATGAATTGATCACTTGCTCT

GTGCTAAGTGTATAAATCATAGATTATTGTATTTAAATAATCGATTTAAA

ATCAAAACAATTTCTGGGTTAAGTTTAATTATCACCATTTTGGGGTTAAG
```

-continued

```
AAAATTAAACTCAGAGGTGAGTTGACTTGTCCAAGGTCACATAGAGGTAG
GGTGGCCAACTCATTCCAGTTTACCTGTGGTTTTTCCAGTTTTAAAACTG
AAATTTTCGTATTTCAGGAACCATTCCCTGCCCCCCAACCTCAGTCCTGG
GTAAACTGGAATGACCCACATCAATGGAAACTAGTAAAGCGAGGATTTAT
TTGGACCCAGTTCTCTTGTCTCCAAACCCAGAGTCCTCTTTGATTCTTTT
GGGTTTGGTTTGCTTTTTTCCTTTTCCTACATTTGACAGTATCTCGAGTG
GTCACAAATGTAAAAAATGTCTAGCATATTGCCTGGCATATAGGAAAAAT
TCAGTAAGTGATAATGATTATCAGTGCTGTGCCAAGCTATGGAGCCAGCC
ATATATATATGGATGTGTGCATATATATATATGATGTGTGTGTATATATA
TATGTCTTTATAAATTTTATGTATTTATTTCTTTCAAAAATATTAAAGTA
TTTGAGAAAATTGAAAAATTAAAAAGTAGGTTTATTACGACTCATGACTT
TAAGTTTAAATATTTTATTTCTGCCCCAAACAAAATTTATTATAATTTTA
CTGTCCTGGTTTTAAGGGAAGGAAACTCATCAATAATATTTTCATCATAT
GCTTTTGAGAAACAAAGTTAACCATTAAGAATGAAACATGAAAACATGTG
AATAGTGGTACAAATTTTTCCTTTTGCTTCAATATGGCTCAGCATGGCAC
TGTCGAATTTTGTCTTTATATAAAATTTTGATATTTTGTTTGTCATAAGC
TTTTTAATTCATTTTTATATTGCACTAAAATATTTTTATCTTGATGACTG
AGGTTTTTTAGTGCTCCCTTAAATTTTGCACCTAAAATGAGTGCCTCAAT
TGTTTTACCCTAACCTCAGCCCATTATTATTTTATCTTAAAACTCAGCAA
ACACCCTAACCTGCTCTCTTACTGAGGAGGCTCGCCCAAGAATAAATGAG
TTCCGTCATTGCCTTTCTTCTCTGACTTTTGGGACCATTTGCTTGGTCTA
GGACCTGAGTTGCAGGTCCAGGAAAGCGTGTACTCTCGAATCCACCCAGG
AGTGCCTGACTACAGTCCTCCTGCAGAGGGCGCTGTGGAGTCCCAGACAC
GAGTGTTAGGTGGAATCGGGCTGATTGCCCATCACGTCTTGCCTTTCCCT
GGCAGTAGGCTTGTTATGAAATCATTGACTTTCTATTTGCCTCTGGGGCT
TAAGCGAATCTGTTACCCTCAAATAACCTATCTGATCTCAGACAAATGCC
AAACAGAGCTCAGTTTCTCTGCCCTGTGGGTGGCCATAAAATCCAGACAA
TTTCCCCCTAGGTGTTTTCGATGGCGCAGCCACAGCTTCTGTGAGATTCG
ATTTCTCCCCAGTTCCCCTGTGGGTCTGAGGGGACCAGAAGGGTGAGCTA
CGTTGGCTTTCTGGAAGGGGAGGCTATATGCGTCAATTCCCCAAAACAAG
TTTTGACATTTCCCCTGAAATGTCATTCTCTATCTATTCACTGCAAGTGC
CTGCTGTTCCAGGCCTTACCTGCTGGGCACTAACGGCGGAGCCAGGATGG
GGACAGAATAAAGGAGCCACGACCTGTGCCACCAACTCGCACTCAGACTC
TGAACTCAGACCTGAAATCTTCTCTTCACGGGAGGCTTGGCAGTTTTTCT
TAGTAAGTTGCGTGGATGGGCCACACTGTCTGAGGCCAGATAAGGCTGTT
CTCTTCCCCTGACCCCCACCCCTCACCCCGTGGACACTTGGAGGAGGGG
AAACTCAGTAAGTCATGCTCTCTTCTTTGAATTCCTAGCTCCTGTGGTCT
CCAGATTTCAGGCCTAAGATGAAAGCCTCTAGTCTTGCCTTCAGCCTTCT
CTCTGCTGCGTTTTATCTCCTATGGACTCCTTCCACTGGACTGAAGACAC
TCAATTTGGGAAGCTGTGTGATCGCCACAAACCTTCAGGAAATACGAAAT
GGATTTTCTGAGATACGGGGCAGTGTGGTACGTAAGCGGGTATCTACCTC
```

-continued

```
TCCTGAAAGCCTTTTCTCTTCCTTCCTTGTCCGTTTCTCTTTCCTGGCAG
TACTGGCAGTGTAATCATAAAAAGAGGCAGGCTGGGGATTCCTTACCCGG
GGGATGTATTCCAAAGAAATAACTGTAGTTCAAATATTTAAAATGTTTTG
GGAAAGGACACCTCCCACTAGTTCTTGGCAGGGAGTGGATGAGAAGTCTT
GATATTGAAGACCCTGGCAGCAGGCACTGACTCATCCTTGCTTGTTTTGT
CTTCTTCTGTTTAGCAAGCCAAAGATGGAAACATTGACATCAGAATCTTA
AGGAGGACTGAGTCTTTGCAAGACACAAAGGTATGTGCTTGGCCCAGACA
AACTCTGGGAGGAGGAGTGGAGTGGGAGCATCTCCATCACCCTGGTCTTG
TCTCTGCTCTCCCCTTTCCCCTCACCAATATACCTGTGGTTTTTTGCAGC
CTGCGAATCGATGCTGCCTCCTGCGCCATTTGCTAAGACTCTATCTGGAC
AGGGTATTTAAAAACTACCAGACCCCTGACCATTATACTCTCCGGAAGAT
CAGCAGCCTCGCCAATTCCTTTCTTACCATCAAGAAGGACCTCCGGCTCT
GTGTGAGTGTGGGTCTTGGGTGACAGGATGCATCTCAGCACACAGCTTCA
ATGGCTTAGCAACTAAACTCTCTTTCCTACCTCCATTTAATGGATGGAGA
AACTGAGTCCAAAAGTTCTAATAATCTGTGTTGAGACATGTGACTAGGTA
ATAAGAACTCAGTTTTATTGACTTTTCGGTATATGTCTAGGCAAAAGT
ACTTTGCAAAGTCTAAAGAACTATAAGATGCTAACTATTTGATATTAATG
ATAACTCTGTTGTCTTTGAAATTATACTTTTTCTGTAGGTGAGGTATCCT
ACAGTATATTAGTGCGTCCTCTGTCTAGGCAGTCAATTAGTAGACCATTG
AGCTTGACCTCAGAATATAGTCTGAATAGGACCTAGGAATTCAATTCTTT
TTTTTTTTTTTCTCAATGGGGGCTCAAAGAGCTCTGGGATAGAGCTCCTA
GACTACAGCTGGGGGTTGTGGGGAGGCCAGATGGGGTACGGGGATGGCAA
ATGCCTTCAGTACTGCCTGCCTATTTCTAAAAAAGAAGTGATGAGTTCCA
TGTTTGAGCCTAAAAGGTGGCTTCCTCTCCTAGCTGATGATGAACTTAAT
GATTCCAAATGTGAGGTCTGAAAGAGCTTTTCTATAGGAATAAGCATCCT
CAGGGTTGTGGGTGAAAGAGTAGAGTTTCTACCTGCTTCATGTCAATGGC
AAAAAATCAGAATCTGTAATATAATCTATTATTCTTTGGGTCCTTTTCAG
CATGCCCACATGACATGCCATTGTGGGGAGGAAGCAATGAAGAAATACAG
CCAGATTCTGAGTCACTTTGAAAAGGTATATGCGACTTTGGCATTGATTG
GGATGGGTGTGTTTTAAGAACTGAGATCATAGGTAGGTGGGATGGTTATT
CACTGTTAGACATCCTGTAGCCTTCAGGTTCATAGCCCTCTGAAATCATG
AGGACCAGCCCTTGCTTTAACCCAGGGGACACCCATCCAGGCTCTAGAGG
AGTACCCTCTCTGGGTGATGCTCTGGAAATGGAAAGGGAATGGCCATGAT
TCCATCAAGTCACTACAGTGACATCTGGATCTTTTAGCTGCACAAACCAG
AGGCAATAGTTTTACAATGTTCACACACTTCTATGTACCTTTGAAAACAC
TCACAATTTCACACACACACCCATGCCATTCAATTTCTCACCTTCACACC
TTCTCATGTCTGCCAGGAAGGCCTGGATTTCACTCCTCACTGACTAAATC
CTACTCATCCTTTAAAGACTCAGCCTGGGCATCACTTTCAGGAAGGTGCT
GGCTCCTTCTCTCAGAGTTAGATGCCTCCCACATCATCTTGTAGGAATTT
CATCCCTTTATTCACCACACTACATTTTAGTTGCCTGTTTTTGCCAGTCT
```

```
CCTCACTCAACTGTGGATAGGGATTGTGCCATTCACCTTTTCATCCCTAA

CCATCAGCTAGGTGATTGGCACAATCAATATCTGTTCAACTGATGTGTGC

ACCGTAGGCAACCCCTACACACACACACAGGCACGTGCACACACACACAC

ACACACGTTTCTTAAAGAAAATAGCTTGATTATTTTGATCTCTGTGATTC

AAGAGTCTTAAGTAGCAGTTTTACTTCTGCTACCCCCTTGCACCTCAGTT

TCTGTACATAAGACCAGGGTGATGAACTCAATGATTTCCCTTCCTTGTGT

GATATCTTGAGATTCTATAACTTCTTTAAGTGCTTCATCTTGAAAAGAAT

GCTCTGCTTACAATTGTCAGCAGACCTATCCATAAAAGAGATAGGTCCTG

GAGCAAATGCTGTCTCATGAATTGCTAACCACATGGGTGTGTCTCTTT

CAGCTGGAACCTCAGGCAGCAGTTGTGAAGGCTTTGGGGGAACTAGACAT

TCTTCTGCAATGGATGGAGGAGACAGAATAGGAGGAAAGTGATGCTGCTG

CTAAGAATATTCGAGGTCAAGAGCTCCAGTCTTCAATACCTGCAGAGGAG

GCATGACCCCAAACCACCATCTCTTTACTGTACTAGTCTTGTGCTGGTCA

CAGTGTATCTTATTTATGCATTACTTGCTTCCTTGCATGATTGTCTTTAT

GCATCCCCAATCTTAATTGAGACCATACTTGTATAAGATTTTTGTAATAT

CTTTCTGCTATTGGATATATTTATTAGTTAATATATTTATTTATTTTTG

CTATTTAATGTATTTATTTTTTTACTTGGACATGAAACTTTAAAAAAATT

CACAGATTATATTTATAACCTGACTAGAGCAGGTGATGTATTTTTATACA

GTAAAAAAAAAAACCTTGTAAATTCTAGAAGAGTGGCTAGGGGGGTTAT

TCATTTGTATTCAACTAAGGACATATTTACTCATGCTGATGCTCTGTGAG

ATATTTGAAATTGAACCAATGACTACTTAGGATGGGTTGTGGAATAAGTT

TTGATGTGGAATTGCACATCTACCTTACAATTACTGACCATCCCCAGTAG

ACTCCCCAGTCCCATAATTGTGTATCTTCCAGCCAGGAATCCTACACGGC

CAGCATGTATTTCTACAAATAAAGTTTTCTTTGCATAACATCTGCTTGGA

GTTTGCAAATGTTTCAAGAGCAGAGACCATGTTGAGGATAAGTTTGAATC

TCATTTCACCCCAGGTCCTCTTGCTCCTTTGAGGAAGAAGATGTAGGAAC

CTCGATCTTCTCTCTCCTGCAGATTTCATCCTCAGCTCTATCTCCTAATT

CATACTGCTCTGACCCCACGACTGCCCTCCTCTCAAAAGGACTGTGACAG

AGTGAGGGGCTTCAGCCATCTCTGCTTTCGCCTCATTGGCTTGGAGCACT

GCCCTTTCTATACCTCTGTTTTCTTTCTCACCCCATACCCTTGCAAGACA

AATTACAATGGGCATGAGGCGCTATTATAAAGGTTAAAAACACACAGGTG

CAAAGTGTAGGTCTAGAGTCTTGCCCAGACAGGTGTATGAGCCCCCTTTT

GAGGCCCTTCCATTTTGGATTCTGTCCAGCCTCAGAGTTTAGGTTGTTAC

CAGATCAAGTCCTTATCTTTGTGTCCAACTATTAAGTCAGTGTTTTCTTT

CCAGGCCCCCTTCAGGTTGAGTGTCCCTGGACACTGAGGAGCCAGAGTTC

TGGCCTGGGCTGGTTCCTTCCTTCTTCCCCCACCTCACTCTGAAGCGCAC

CCCCAATTTAGTTGCTTAGTTTTCTCAGTCTCAGAAACAACAGTCTCAGG

CTGATTCCCTGGGTCCTAAAGATAACTCTCCTTACTGCTTTAATTTCTAC

TCCCTGTTCTTAGCCTGGGCCCTGATATAGTTTCAATGACTTTAACTTTT

GATAACTCTCATTATACAAGTAACAGCTGCCCAACAGAAAAGAAATTTTG

GAAGAAAACAGAAATATAAAGAAGAAAATTAAAATCACCCATAATCTCAC
```

```
CACCCTCAGACAACCACTTTTAAACATTTATGCTTATTTTTTCCAGATAT

TTTTTGATGGGTTCAAATCATGACTCAGCTCTCA
```

An amino acid sequence for target antigen IL-20 is reproduced below:

(SEQ ID NO: 6)
Accession No. AAK84423.1,
MKASSLAFSLLSAAFYLLWTPSTGLKTLNLGSCVIATNLQEIRNGFSEIR

GSVQAKDGNIDIRILRRTESLQDTKPANRCCLLRHLLRLYLDRVFKNYQT

PDHYTLRKISSLANSFLTIKKDLRLCHAHMTCHCGEEAMKKYSQILSHFE

KLEPQAAVVKALGELDILLQWMEETE

D. C-C Motif Chemokine 19 (CCL19)

Target antigen C-C motif chemokine 19 (CCL19), also known as "MIP-3-beta Recombinant Human Protein," is a bioactive chemokine. Target antigen C-C motif chemokine: 19 is known to have the following antigenic fragments, all of which are considered to be covered by this present invention as potential target antigens. AA residues 1 to 21, "signal peptide"; 22 to 98; "mature chain"; 26 to 29 "beta-strand region"; 27 to 87 "chemokine_CC_DCCL, subgroup based on the presence of a DCCL motif involving two N-terminal cysteine residues"; 42 to 49 "beta-strand region"; 51 to 53 "hydrogen bonded turn"; 59 to 64 "beta-strand region"; 69 to 72 "beta-strand region"; 74 to 76 "beta-strand region"; 77 to 90 "helical region."

An amino acid sequence for C-C motif chemokine 19 is reproduced below:

(SEQ ID NO: 7)
Accession No. Q99731.1,
MALLLALSLLVLWTSPAPTLSGTNDAEDCCLSVTQKPIPGYIVRNFHYLL

IKDGCRVPAVVFTTLRGRQLCAPPDQPWVERIIQRLQRTSAKMKRRSS

Detection and Diagnostic Methods

In one embodiment, the present invention provides a method for detecting Early-Stage PD autoantibody biomarkers in a subject in need of such detection comprising obtaining an immunoglobulin-containing biological sample from the subject, and performing an assay to determine the presence or absence of one or more of the biomarkers in the biological sample.

In another embodiment, the present invention provides a method for diagnosing Early-Stage PD in a subject in need of such diagnosis comprising obtaining an immunoglobulin-containing biological sample from the subject, performing an assay to determine the presence or absence of one or more Early-Stage PD autoantibody biomarkers in the biological sample, and diagnosing Early-Stage PD if one or more PD diagnostic biomarkers are present.

In a preferred embodiment, the subject is a human subject. In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. Serum and plasma samples may be obtained by centrifugation methods known in the art. Sputum and saliva samples may be collected by methods known in the art. The biological samples may be diluted with a suitable buffer before conducting the assay. In a preferred embodiment, the biological sample is serum, plasma, or whole blood.

Assays to determine the presence or absence of one or more Early-Stage PD autoantibody biomarkers in the biological sample are performed by contacting the sample with one or more antigens that are specific for an Early-Stage PD autoantibody biomarker under conditions that allow an immunocomplex of the antigen and the antibody to form, and detecting the presence of the immunocomplex.

An antigen may comprise a protein antigen listed in Table 1 above, or a polypeptide or peptide fragment thereof containing one or more epitopes recognized by the Early-Stage PD autoantibody biomarker, or an epitope peptidomimetic that is recognized by the Early-Stage PD autoantibody biomarker. Peptidomimetics include, for example, D-peptides, peptoids, and (3-peptides. The antigens may be purified from natural sources, or produced recombinantly or synthetically by methods known in the art, and may be in the form of fusion proteins. The antigens may be produced in vitro using cell-free translation systems. In one preferred embodiment, the antigens are produced in a mammalian or insect expression system to ensure correct folding and function. All of these methods may be automated for high throughput production.

Assays and conditions for the detection of immunocomplexes are known to those of skill in the art. Such assays include, for example, competition assays, direct reaction assays and sandwich-type assays. The assays may be quantitative or qualitative. In one preferred embodiment, the assay utilizes a solid phase or substrate to which the antigens are directly or indirectly attached, such as a microtiter or microassay plate, slide, magnetic bead, non-magnetic bead, column, matrix, membrane, or sheet, and may be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate preferably comprises a plurality of individually addressable antigens immobilized on the surface. The individually addressable antigens are preferably immobilized on the surface to form an array. The substrates may be used in suitable shapes, such as films, sheets, or plates, or may be coated onto or bonded or laminated to appropriate inert carriers, such as paper, glass, plastic films, or fabrics. In a preferred embodiment, the substrate is a slide or a bead.

Methods for attaching the antigens to the support or substrate are known in the art and include covalent and non-covalent interactions. For example, diffusion of applied proteins into a porous surface such a hydrogel allows non-covalent binding of unmodified protein within hydrogel structures. Covalent coupling methods provide a stable linkage and may be applied to a range of proteins. Biological capture methods utilizing a tag (e.g., hexahistidine/Ni-NTA or biotin/avidin) on the protein and a partner reagent immobilized on the surface of the substrate provide a stable linkage and bind the protein specifically and in reproducible orientation.

In one preferred embodiment, the antigens are coated or spotted onto the support or substrate such as chemically derivatized glass, or a glass plate coated with a protein binding agent such as, but not limited to, nitrocellulose.

In one preferred embodiment the antigens are provided in the form of an array, and preferably a microarray. Protein microarrays are known in the art and reviewed for example by Hall et al. (2007) *Mech Ageing Dev* 128:161-167 and Stoevesandt et al. (2009) *Expert Rev Proteomics* 6:145-157, the disclosures of which are incorporated herein by reference. Microarrays may be prepared by immobilizing purified antigens on a substrate such as a treated microscope slide using a contact spotter or a non-contact microarrayer. Microarrays may also be produced through in situ cell-free synthesis directly from corresponding DNA arrays.

Suitable methods for external production and purification of antigens to be spotted on arrays include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

Suitable methods for in situ ("on-chip") protein production are disclosed, for example, by Ramachandran et al. (2006) *Methods Mol. Biol* 2328:1-14 and He et al. (2008) *Curr. Opin Biotechnol* 19:4-9.

Other methods by which proteins are simultaneously expressed and immobilized in parallel on an array surface are also known in the art and may be used in accordance with the present invention. For example, in the Protein In Situ Arrays (PISA) method (He et al. (2001) *Nucleic Acids Res* 29:e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or *E. coli* S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran et al. (2004) *Science* 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate pure protein arrays on a separate surface from the DNA, and also can produce multiple copies of a protein array from the same DNA template (He et al. (2008) *Nature Methods*, 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified antigens of the invention that are produced and purified externally may be spotted onto a microarray substrate using a flexible protein microarray inkjet printing system (e.g., ArrayJet, Roslin, Scotland, UK) to provide high quality protein microarray production. The precise rows and columns of antigens may be converted to detectable spots denoting both the presence and amount of diagnostic biomarkers that have been bound.

The production of the microarrays is preferably performed with commercially available printing buffers designed to maintain the three-dimensional shape of the antigens. In one preferred embodiment, the substrate for the microarray is a nitrocellulose-coated glass slide.

The assays are performed by methods known in the art in which the one or more antigens are contacted with the biological sample under conditions that allow the formation of an immunocomplex of an antigen and an antibody, and detecting the immunocomplex. The presence and amount of the immunocomplex may be detected by methods known in the art, including label-based and label-free detection. For example, label-based detection methods include addition of a secondary antibody that is coupled to an indicator reagent comprising a signal generating compound. The secondary antibody may be an anti-human IgG antibody. Indicator reagents include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase, horseradish peroxidase and beta-galactosidase. Methods of label-free detection include surface plasmon resonance, carbon nanotubes and nanowires, and interferometry. Label-based and label-free detection methods are known in the art and disclosed, for example, by Hall et al. (2007) and by Ray et al. (2010) Proteomics 10:731-748. Detection may be accomplished by scanning methods known in the art and appropriate for the label used, and associated analytical software.

In one preferred embodiment of the present invention, fluorescence labeling and detection methods are used to detect the immunocomplexes. Commercially available slide scanners (e.g. the Genepix 4000B slide scanner (Molecular Devices, Inc.) with associated analytical software may be used. In one preferred embodiment, the immunocomplex is probed with fluorescent-labeled (e.g., Alexa-Fluor (Invitrogen)) anti-human antibody and the intensity of fluorescence at each protein spot is measured using a microarray scanner. Commercially available software (e.g. GenePix Pro 5.0 software (Axon instruments)) may be used to extract the net median pixel intensities for individual features from the digital images produced by the scanner. Data may be normalized by comparing median values of multiple identical control spots in different regions of the same array.

Detection of diagnostic immunocomplexes is indicative of the presence of Early-Stage PD autoantibody biomarkers in the biological sample, and thus a positive diagnosis of Early-Stage PD.

The results of the method described above can provide an Early-Stage PD diagnostic biomarker profile for the patient that is useful to diagnose Early-Stage PD and optimize a treatment regimen for PD. The method also can be used for identifying a subject who has or is suffering from developing PD without knowledge, wherein the subject can be identified if one or more of the Early-Stage PD autoantibody biomarkers is present.

In at least another embodiment, a diagnostic system for detecting an Early-Stage PD autoantibody biomarker in a subject who has or is at risk for developing Parkinson's Disease by (a) obtaining an immunoglobulin-containing biological sample from the subject, (b) conducting an immunoassay to detect at least four target antigens or antigenic fragments thereof specific for Early-Stage PD, (c) detecting the presence or absence of an immunocomplex, wherein the presence of an immunocomplex is indicative of the presence of the Early-Stage PD autoantibody biomarker in said patient and absence of such immunocomplex is indicative of absence of Early-Stage PD (d) generating a report identifying said patients who have Early Stage PD or are at risk of developing Early Stage PD and (e) optimizing the treatment plan in patients in need thereof by administering proper anti-Parkinson's treatment regimen.

Substrates and Microarrays

In yet another embodiment, the present invention provides a substrate on which one or more antigens that are specific for an Early-Stage PD autoantibody biomarker are immobilized. The present invention also provides, in another embodiment, a microarray comprising a substrate on which one or more antigens that are specifically bound by an Early-Stage PD autoantibody biomarker are immobilized. The substrates and microarrays may be made as described hereinabove and are useful for creating Early-Stage PD diagnostic biomarker profiles and for the diagnosis of Early-Stage PD. An antigen may comprise a protein antigen listed in Table 1, or a polypeptide or peptide fragment thereof containing one or more epitopes recognized by the Early-Stage PD autoantibody biomarker, or an epitope peptidomimetic that is recognized by the PD diagnostic biomarker. Peptidomimetics include, for example, D-peptides, peptoids, and β-peptides. The substrate and microarrays may contain, as the antigen, at least one of the protein antigens listed in Table 1 or fragments thereof containing one or more epitopes recognized by the Early-Stage PD autoantibody biomarker.

In another embodiment, the substrate and microarrays may contain, as the antigen, at least one of the protein antigens listed in Table 1 or a polypeptide or peptide fragment thereof containing one or more epitopes recognized by the Early-Stage PD diagnostic biomarker, or an epitope peptidomimetic that is recognized by the Early-Stage PD diagnostic biomarker. Peptidomimetics include, for example, D-peptides, peptoids, and β-peptides. In another preferred embodiment of the present invention, the substrate and microarrays contain at least two, or at least three, or at least four, or at least five, or at least six, or at least seven, or at least eight, or at least nine, or all of the protein antigens listed in Table 1 or polypeptides or peptide fragments thereof containing one or more epitopes recognized by the Early-Stage PD autoantibody biomarker, or epitope peptidomimetics that are recognized by the Early-Stage PD autoantibody biomarkers listed in Table 1.

Microarray may be prepared on a glass surfaces with a variety of coatings including but not limited to nitrocellulose, FAST™, FullMoon™, SuperEpoxy™, SuperAldehyde™, SuperNHS™, Ni-NTA, PATH, Nextirion, Nexterion H thin film, epoxysilane or aldehydesilane or other similar coatings. Those of ordinary skill in the art can appreciate the equivalent coatings that can be employed as the suitable substrate. In some embodiments, the substrate can be a nitrocellulose-coated glass slide.

Besides the protein antigen in Table 1, or a polypeptide or peptide fragment thereof, many other protein antigens and polypeptides or peptide fragments thereof can be included in substrates or microarrays of this invention. Examples of these other protein antigens include those disclosed in US20140364328, WO2014018903, WO2013023144, WO2013010003, and WO2011142900, the contents of which are incorporated by reference in their entireties. These documents disclose additional markers for PD and markers for other disorders such as other neurodegenerative diseases and certain cancers. These substrates and microarrays are useful for profiling subjects or patents suspected of having one or more of these conditions and disorders.

In another embodiment, the methods of using the presently disclosed microarray requires detection of at least 4 complex formations between at least 4 autoantigens and at least 4 autoantibodies, wherein formation of such complex formations indicates the existence of Early Stage Parkinson's disease. In another embodiment, methods of establishing the correlation between the autoantibodies and Early Stage Parkinson's are described. In yet another embodiment, methods of identifying and screening candidate therapeutic regimens and anti-Parkinson's therapeutic agents are described that would reduce the associated biomarkers, degree of complex formation between the instant biomarkers and their respective antigens. In another embodiment, such candidate agents are capable of reducing the disease associated biomarkers, inhibiting or reducing the formation of autoantibody and their target autoantigens.

Diagnostic Kits

In a further embodiment, the present invention provides a kit for detecting Early-Stage PD-specific antibodies in a sample. A kit comprises one or more antigens that are specific for an Early-Stage PD autoantibody biomarker and means for determining binding of the antigen to the biomarker in the sample. The kit may also comprise packaging material comprising a label that indicates that the one or more antigens of the kit can be used for the identification of PD. Other components such as buffers, controls, detection reagents, and the like known to those of ordinary skill in art may be included in such the kits. The kits are useful for detecting Early-Stage PD autoantibody biomarkers and for diagnosing PD.

A kit may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target can be added to individual tubes or substrates and assay carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: anticoagulants (e.g., EDTA and heparin), reagents (including buffers) for lysis of cells, divalent cation chelating agents or other agents that inhibit unwanted proteases, control antibodies for use in ensuring that the components of reactions are functioning properly, and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

Treatment Methods

Until now, prior art treatment methodologies of PD rely primarily on conclusions derived from extensive subjective assessments which, in turn, are dependent on the presentation of characteristic symptoms. However, these presentations are often apparent only after the disease is well underway and the brain has already sustained considerable damage to vital brain cells. In at least one aspect of the present invention, early diagnosis of PD based on the immune system's response to an early stage of the disease means provides a conclusive diagnosis long before symptoms emerge and too much brain damage has occurred.

In at least one embodiment, treatments including prophylactic measures are described in patients with a plasma profile indicative of early stage PD. In another embodiment, methods of treatment of early stage PD are described comprising diagnosing patients suffering from early stage PD and treating said patients in accordance to proper treatment regimen. In at least one embodiment, such treatments are administered before the disease has progressed past the point of therapeutic efficacy. In diseases with exceptionally long prodromal periods, early diagnosis would allow patients to avail themselves of treatments much sooner than was previously possible, altering the traditional course of the disease in their favor.

Proper treatment regimens may include but are not limited to dietary modifications to reduce neuronal oxidative stress, daily physical exercise, drug treatment including identification of suitable subjects for enrollment into clinical trials. In at least one embodiment, patients diagnosed or detected with early stage PD may start low dose anti-Parkinson's agents, including antioxidants such as tocopherol.

In at least one embodiment, the anti-Parkinson's agents may include levodopa preparations, and for others, an initial prescription may be given for one of the agonists, an MAO inhibitor or an anticholinergic. The choice of drug treatment depends on many variables including symptom presentation, other concurrent health issues (and the medications being used to treat them) and a person's age, and symptomatology, prevalence of existing biomarkers and frequency of factors such as patient's metabolism, and life style. In at least one embodiment, the specific medication regimen includes low dose Carbidopa/levodopa combination therapy, dopamine agonists, anticholinergics, MAO-inhibitors, COMT inhibitors or other known treatment methods in the art. Low dose treatments may include dosing ranges that is from 10 to 99%, or 15-95%, 30-90%, or 45-75% of the normal and/or regulatory agency approved doses for treatment of Parkinson's.

Accordingly, in some embodiments of the present invention, upon being diagnosed as having Early-Stage PD, a patient is administered one or more anti-Parkinsonian agent. "Anti-Parkinsonian agent" as used herein is defined as any therapeutic compound or composition that is used to prevent, treat, or mitigate Parkinson's Disease or any symptoms associated with Parkinson's Disease, and is specifically intended to cover at least the following examples.

The most widely utilized therapy for treatment PD involves administering therapeutically effective amounts of levodopa (L-dopa) in one or more formulations or compositions, such as levocarb (carbidopa/levodopa). Methods for preparing L-dopa and L-dopa prodrugs are known in the art, as well as their use and formulation may be found at, for example, U.S. Pat. Nos. 3,686,409, 3,878,043, 4,962,223, 4,983,400, 5,607,969 7,671,089, 8,735,382, and US Patent Publication Nos. US/2007/0027216 and US/2008/0255235, incorporated by reference herein in their entirety. Levocarb may be administered, for example, through a continuous infusion. Continuous infusion may be preferable, for example, in those patients who have fluctuation in their response to levocarb. Blood levels of carbidopa and levodopa remain constant in continuous infusion cases. Side effects of L-dopa and levocarb include dyskinesia (LID), and tolerance to L-dopa may build up over time. Administration of levocarb is generally between 0.01 mg and 1 g daily, generally between 50 mg to 500 mg., with a general starting dosage such as 100 mg L-dopa/25 mg carbidopa 3× daily, although administration may be changed over time according to patient's physiological characteristics.

Other therapeutic methods and treatments include dopamine agonists, including but not limited to pramipexole, ropinirole, and rotigotine. Dopamine agonists may be either long-acting or short-acting, for example Apo morphine. Dopamine agonists do not become metabolized into dopamine such as L-dopa, and as such may not be generally as effective. However, such agonists may last longer than L-dopa and may be used in combination with L-dopa, particularly where L-dopa is not administered in a continuous infusion. Side-effects for dopamine agonists are similar to L-dopa, but may also include hallucinations and other compulsive behaviors. Dosages for dopamine agonists are generally increased over time, and may be administered in a variety of ways, such as tablets, capsules, or by injection, continuous infusion, or by patches.

MAO-B inhibitors are another class of compounds suitable for treatment of Parkinson's. These may include, for example, selegiline and rasagiline. MAO-B inhibitors prevent the breakdown of dopamine by mimicking monoamine oxidase B (MAO-B). MAO-B inhibitors may be administered alongside L-dopa and/or levocarb, but carry similar risks of side-effects as with dopamine agonists. MAO-B inhibitors carry additional risks beyond those of dopamine agonists, and are not used in combination with anti-depressants or other narcotics due to potentially life-threatening reactions. MAO-B inhibitors may be administered via standard oral routes, such as in disintegrating tablets, and may be administered via other routes known in the art. MAO-B inhibitor dosage may be between 0.01 and 10 mg dosages, with ordinary dosages being between 0.5 mg and 1 mg doses given once or twice per day.

Other treatment methods include COMT inhibitors. Entacapone is the primary medication for this class, although tolcapone is an available therapeutic compound, which is not widely utilized due to risk of liver failure. COMT inhibitors block the enzyme catechol-O-methyltransferase (COMT), which is an enzyme that breaks down dopamine. COMT inhibitors, like L-dopa and levocarb, may result in dyskinesia (LID). Entacapone is generally administered between 50 and 2,000 mg/day, with dosage being one 200 mg tablet administered (optionally) with L-dopa/levocarb from once a day up to about 8 times a day.

Further potential pharmaceutical-based treatment methods include anticholinergics, and amantadine, but these are not used as often today because of the advance of preferable medications, such as those described herein. However, amantadine may still be prescribed in order to provide short-term relief of symptoms, particularly in Early-Stage PD, even though amantadine is generally recognized to be less effective than L-dopa at later stages. Thus, administration of Amantadine may be a first choice therapy after a positive diagnosis by the compositions, methods and kits of the present invention. Amantadine may be administered according to a number of routines known in the art.

Antibody-based therapies are another potential possibility, and while no FDA approved biologics for treatment of Parkinson's exist as of the time of this invention, potential candidates exist, including but not limited to LRRK2 (leucine-rich repeat kinase 2) antibodies. Additional antibodies include alpha-synuclein antibodies. Alpha-synuclein was the first gene to be linked with PD, and is a major component of Lewy bodies and is believed to be a promising link for PD pathogenesis. DJ-1 antibodies remain another area of interest, and are thought to act as a sensor for oxidative stress in the cell. These antibodies described herein may be human antibodies, humanized antibodies, murine antibodies, chimeric antibodies, rat antibodies, and other antibody constructs and may be administered according to methods known in the art.

Non-pharmaceutical or biologic based therapies include experimental treatments such as deep brain stimulation (DBS). An electrode is inserted through an opening in the skull and implanted within a specific brain area to which electrical impulses are provided. This may provide relief to the patient suffering from PD.

EXAMPLES

Example 1

This example describes material and methods used in Examples 2-7 below.

Approval for the use of serum samples in this study was obtained from the University of Medicine and Dentistry of New Jersey—School of Osteopathic Medicine and the Rowan-Stratford Institutional Review Boards.

Human Samples

103 Early-Stage PD samples were obtained from the Michael J. Fox Foundation (New York, N.Y.) in coordination with the Parkinson Study Group (Boston, Mass.). These samples came from subjects participating in the DATATOP study, which was a clinical trial investigating the potential beneficial effects of two anti-oxidative therapies, deprenyl and tocopherol, to delay the time at which patients progress to disability requiring levodopa treatment (DATATOP: a multicenter controlled clinical trial in early Parkinson's disease. Parkinson Study Group. *Archives of Neurology* 46, 1052-1060 (1989)). Diagnosis of PD was made with follow-up with 90% confidence by the DATATOP clinical investigators, and each patient was determined to have a Hoehn and Yahr scale score ranging from 1 to no greater than 2. Twenty-nine mild-moderate PD and 50 mild-moderate Alzheimer's disease serum samples were obtained from Analytical Biological Systems, Inc. (Wilmington, Del.). Thirty stages 0-2 breast cancer (BC) serum samples were obtained from Asterand, Inc. (Detroit, Mich.), and 30 multiple sclerosis (MS) patient serum samples were obtained from BioServe Biotechnologies Ltd (Beltsville, Md.). Healthy age- and sex-matched control serum samples were obtained from several sources: 40 from Analytical Biological Systems, Inc.; 65 from BioServe Biotechnologies Ltd.; 28 from Asterand Inc.; and 23 from The New Jersey Institute for Successful Aging at Rowan University (Stratford, N.J.). All samples were handled using standard procedures and stored at −80° C. until use. Demographic characteristics of the study population are displayed in Table 4.

Human Protein Microarrays

To identify autoantibodies in human sera, Invitrogen's ProtoArray v 5.0 Human Protein Microarrays (Cat. No. PAH0525020, Invitrogen, Carlsbad, Calif., USA), each containing 9,486 unique human protein antigens (www.invitrogen.com/protoarray), was used. All proteins were expressed as GST fusion proteins in insect cells, purified under native conditions, and spotted in duplicate onto nitrocellulose-coated glass slides. Arrays were probed with serum and scanned according to the manufacturer's instructions. Briefly, microarrays were blocked using Blocking Buffer (Cat. No. PA055, Invitrogen) and each was incubated with serum diluted to 1:500 in washing buffer. After washing, arrays were probed with anti-human IgG (H+L) conjugated to AlexaFluor 647 (Cat. No. A-21445, Invitrogen) diluted 1:2,000 in washing buffer. Arrays were then washed, dried, and immediately scanned with a GenePix 4000B Fluorescence Scanner (*Molecular Devices*, Sunnyvale, Calif., USA).

Microarray Data Analysis

Fluorescence data was acquired by aligning the Genepix Array List (GAL) onto the microarray using the Genepix Pro analysis software. The resulting Genepix Results (GPR) files were imported into Invitrogen's Prospector 5.2 for analysis. The "group characterization" and "two—group comparison" features in the IRBP Toolbox within Prospector then enabled M-statistical analysis of differential autoantibody expression between the two groups. Autoantibodies were sorted into descending order by difference of prevalence between early stage PD and control groups, and the top 50 most differentially expressed autoantibodies were chosen as potential diagnostic biomarkers. All data is MIAME compliant and raw data has been deposited in a MIAME compliant database (GEO).

The predictive classification accuracy of the selected biomarkers in the Training Set, Testing Set, and then in both sets combined was tested with Random Forest (RF), another significance algorithm run as an R package (v 4.6-10), using the default settings. Selected biomarkers were tested with the RF model and classification accuracy is reported in a confusion matrix and misclassifications as an Out-Of-Bag (OOB) error score. Receiver operating characteristic curves (ROCs) were generated using R(3.02) packages ROCR(v 1.0-5) and pROC(v 1.7.3).

Example 2

Selection of a Panel of Autoantibody Biomarkers for Early-Stage PD Diagnosis

Previously published data from inventors' laboratory has highlighted the potential utility of autoantibodies as blood-based biomarkers for diagnosing mild-moderate PD (Han et al. *PloS one* 7, e32383 (2012)). Here, the same strategy was used to search for biomarkers useful for Early-Stage PD detection (FIG. 1). To achieve this, 103 Early-Stage PD serum samples from patients with a clinical diagnosis of PD at 90% confidence and 111 age- and sex-matched control samples (total n=214) were randomly separated into a Training Set and Testing Set (Table 4). The Training Set contained 52 Early-Stage PD samples and 56 controls, while the Testing Set contained 51 Early-Stage PD samples and 55 controls. Human protein microarrays containing 9,486 antigens were probed with Training or Testing Set sera. Using Prospector analysis software, 2,470 autoantibodies with a significantly (p<0.05) higher prevalence in the Early-Stage PD group compared to controls were identified in the Training Set as potential diagnostic biomarkers. From this list, the top 50 most differentially expressed autoantibodies in the Early-Stage PD group were chosen as a working diagnostic panel of biomarkers (Table 1).

Example 3

Verification of Biomarkers Via Training and Testing Set Analysis

Figure 2A:
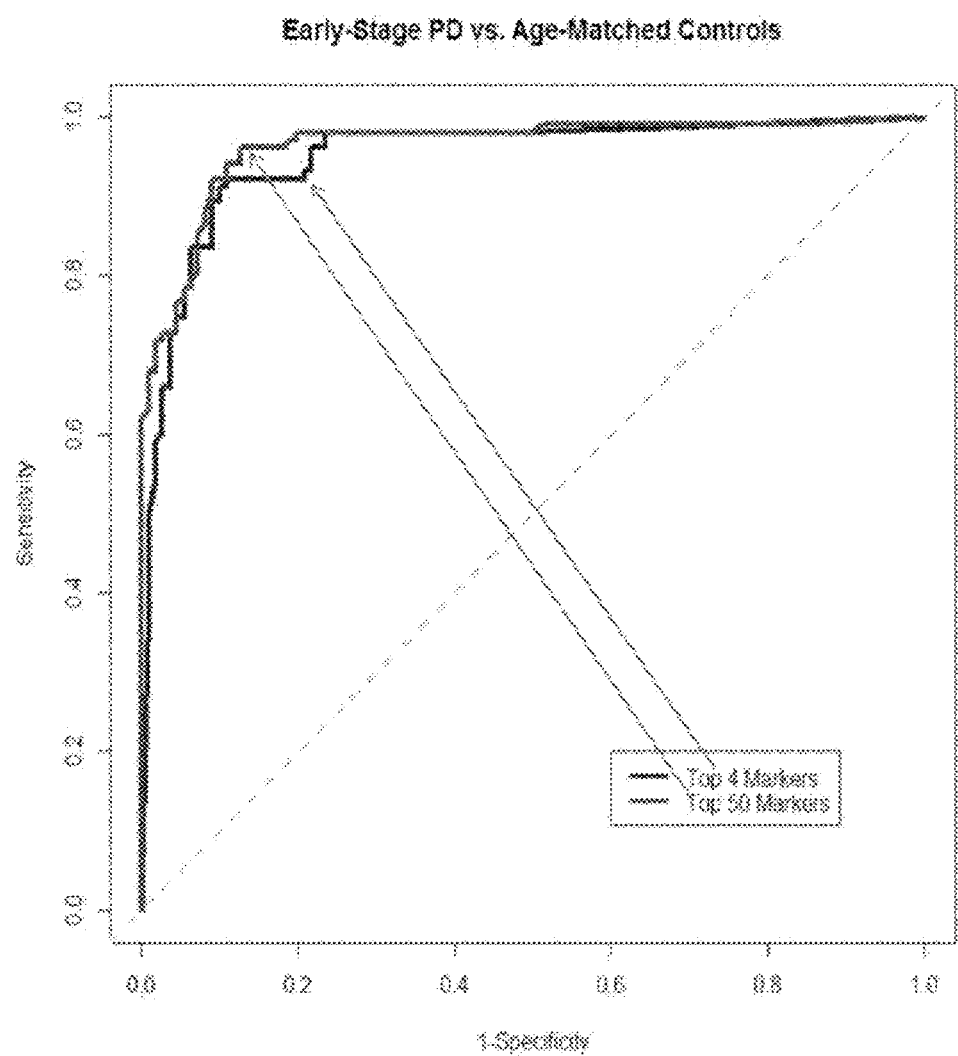
FIGS. 2a and 2b are Receiver Operating Characteristic (ROC) curves showing assessment of autoantibody biomarkers for detection of Early-Stage PD. ROC curves are used to assess the utility of diagnostic tests; the further the plotted line extends into the upper left corner of the box, the better the utility of the diagnostic and the closer the Area Under the Curve (AUC) approaches a value of 1.0, which is the best result a diagnostic test can achieve. 2a shows comparison of Early-Stage PD (n=103) vs. age-matched controls (n=111) using a panel of 50 (dark black line) or 4 (grey line) biomarkers show that these biomarker panels can be used to detect Early-Stage PD with relatively high overall accuracy. The dashed line represents the line of no discrimination, meaning that the diagnostic would have no utility if the plot followed this line. The ROC AUC, sensitivity, and specificity values for the 50 and 4 biomarkers are shown in Table 3.

The top 50 autoantibody biomarkers chosen from the Training Set as the Early-Stage PD diagnostic panel were then re-verified as significant predictors by Random Forest (RF) (Breiman L (2001) Random Forests. Machine Learning 45: 5-32). Upon evaluation of the Training Set samples (n=108; 52 Early-Stage PD, 56 controls) utilizing the 50 selected biomarkers, Early-Stage PD subjects were distinguished from age- and sex-matched controls with a 91.9% prediction accuracy and an Out-of-Bag (OOB) error of 8.1%. The same 50 biomarkers were then used to classify Early-Stage PD in the Testing Set, which was not involved in biomarker selection. RF was able to correctly classify Early-Stage PD in Testing Set subjects (n=106; 51 early stage PD, 55 controls) with an overall accuracy of 87.9% and an OOB error of 12.1%. Combining both Training and Testing Set samples, RF successfully distinguished Early-Stage PD from controls with an overall accuracy of 89.2% and an OOB error of 10.8% (Table 2). The diagnostic utility of the panel of 50 selected biomarkers for distinguishing Early-Stage PD subjects from age-matched controls was also interpreted using Receiver Operating Characteristic (ROC) curve analysis (Zou et al. *Circulation* 115, 654-657 (2007) (FIG. 2a). The ROC area under the curve (AUC) for this comparison was 0.93, indicating excellent classification accuracy (Table 3). The diagnostic sensitivity, specificity, and positive and negative predictive values for the 50 biomarkers are also shown (Table 2).

TABLE 2

Diagnostic results using a panel of 50 Early-Stage PD autoantibody biomarkers. The performance of the top 50 Early-Stage PD autoantibody biomarkers was assessed using RF. Combining both Training and Testing Set samples, RF successfully distinguished Early-Stage PD (N = 103) from age- and sex-matched controls, age-matched plus younger controls, mild-moderate PD, mild-moderate AD, multiple sclerosis and breast cancer with high overall accuracies. PPV, positive predictive value; NPV, negative predictive value.

| | Early-Stage PD (n = 103) vs. | | | | |
|---|---|---|---|---|---|
| | Age Matched Controls | Mild-Moderate PD | Mild-Moderate AD | Multiple Sclerosis | Breast Cancer |
| n | 111 | 29 | 50 | 30 | 30 |
| Sensitivity % | 94.2 | 98.1 | 98.1 | 98.1 | 98.1 |
| Specificity % | 84.7 | 100.0 | 98.0 | 93.3 | 96.7 |
| PPV % | 85.1 | 100.0 | 99.0 | 98.1 | 99.0 |
| NPV % | 94.0 | 93.6 | 96.1 | 93.3 | 93.6 |
| Overall Accuracy % | 89.2 | 98.5 | 98.0 | 97.0 | 97.7 |
| Overall Error % | 10.8 | 1.5 | 2.0 | 3.0 | 2.3 |

TABLE 3

ROC curve analysis of diagnostic results. ROC curve analyses was used to assess the diagnostic utility of the panels of 50 and four selected biomarkers for distinguishing Early-Stage PD subjects from age-matched controls from the subject groups listed. Areas under the curve (AUC) at 95% confidence are listed along with values for sensitivity and specificity derived from the ROC curve output data.

| | 50 Markers | | | 4 Markers | | |
|---|---|---|---|---|---|---|
| Early-Stage PD (n = 103) vs. | AUC (95% CI) | Sensitivity (95% CI) | Specificity (95% CI) | AUC (95% CI) | Sensitivity (95% CI) | Specificity (95% CI) |
| Age Matched Controls (n = 111) | 0.93 (.88-.99) | 0.92 (.84-.98) | 0.87 (.78-.94) | 0.92 (.86-.97) | 0.84 (.74-.94) | 0.87 (.78-.94) |
| Age Matched and Younger Controls (n = 156) | 0.96 (.93-.98) | 0.91 (.85-.96) | 0.94 (.90-.97) | 0.96 (.93-.98) | 0.91 (.85-.96) | 0.94 (.90-.97) |
| Mild-Moderate PD (n = 29) | 0.98 (.97-1) | 0.98 (.95-1) | 1.00 | 0.99 (.97-1) | 0.98 (.95-1) | 1.00 |
| Mild-Moderate AD (n = 50) | 0.99 (.97-1) | 0.98 (.95-1) | 1.00 | 0.99 (.97-1) | 0.98 (.95-1) | 0.98 (.94-1) |
| Multiple Sclerosis (n = 30) | 0.98 (.97-1) | 0.98 (.95-1) | 1.00 | 0.99 (.97-1) | 0.98 (.95-1) | 1.00 |
| Breast Cancer (n = 30) | 0.99 (.98-1) | 0.98 (.93-1) | 1.00 | 0.99 (.97-1) | 0.98 (.95-1) | 0.97 (.90-1) |

TABLE 4

Subject demographics. For each disease group the number of individuals (n), age, range of age, gender, and ethnicity are listed. For the Early-Stage PD subjects, the Unified Parkinson's Disease Rating Scale (UPDRS) and Hoehn and Yahr scores are included as indices of PD severity.

| | | Age | | Sex | Ethnicity | | Hoehn & |
|---|---|---|---|---|---|---|---|
| Group | n | (Years) | (Range) | (% Male) | (% Caucasian) | UPDRS | Yahr |
| Parkinson's disease | 132 | 65.1 ± 10.3 | 37-88 | 57 | 89 | — | — |
| Early-Stage | 103 | 62.7 ± 9.3 | 37-79 | 58 | 98 | 38.1 ± 16.8 | 2.1 ± 0.6 |
| Mild-Moderate | 29 | 74.3 ± 9.0 | 53-88 | 55 | 55 | — | — |
| Controls | 156 | 55.0 ± 15.6 | 19-87 | 56 | 76 | — | — |
| Age-Matched | 111 | 63.1 ± 8.4 | 51-87 | 56 | 78 | — | — |
| Non Age-Matched | 45 | 34.9 ± 10.2 | 19-50 | 49 | 71 | — | — |
| Alzheimer's disease | 50 | 78.5 ± 8.8 | 61-97 | 42 | 88 | — | — |

TABLE 4-continued

Subject demographics. For each disease group the number of individuals (n), age, range of age, gender, and ethnicity are listed. For the Early-Stage PD subjects, the Unified Parkinson's Disease Rating Scale (UPDRS) and Hoehn and Yahr scores are included as indices of PD severity.

| Group | n | Age (Years) | (Range) | Sex (% Male) | Ethnicity (% Caucasian) | UPDRS | Hoehn & Yahr |
|---|---|---|---|---|---|---|---|
| Multiple Sclerosis | 30 | 51.0 ± 9.2 | 36-67 | 33 | 97 | — | — |
| Breast Cancer | 30 | 46.9 ± 5.8 | 32-54 | 0 | 97 | — | — |

Example 4

Minimum Number of Autoantibodies Required for Accurate Early-Stage PD Diagnosis

Figure 4:
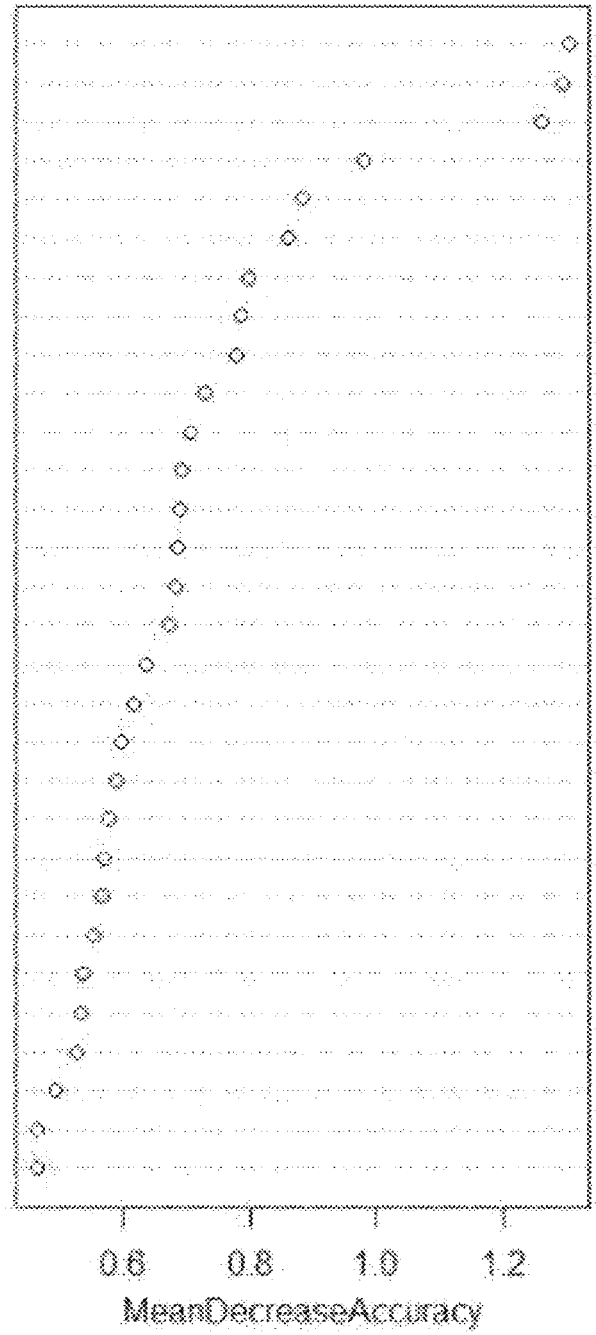
FIG. 4 is a diagram showing effect of younger controls on biomarker selection and diagnostic importance. Gini plots demonstrating the relative importance of 30 of the top 50 biomarkers to the RF classification decision when comparing age-matched controls plus younger healthy controls. Biomarkers are sorted according to decreasing relative importance from top to bottom, with the relative impact of each biomarker to the RF classification decision indicated by the extent of deflection of the indicator point to the right side of the plot. Note that the identities of the top 4 biomarkers shown in both plots are the same for both panels.

To determine the minimum number of autoantibody biomarkers required to achieve the best diagnostic accuracy, biomarkers were sorted according to decreasing relative importance from top to bottom in a Gini Plot, with more favorable diagnostic capability reflected by a greater mean decrease in accuracy (FIG. 4). Biomarkers with the lowest mean decrease in accuracy were successively removed until the overall diagnostic accuracy began to decline significantly. Using this approach, a panel of four biomarkers (top four biomarkers in Table 1) was found to be the minimum number required to maintain an effective diagnostic accuracy (ROC AUC=0.92; sensitivity=0.84; specificity=0.87) for distinguishing Early-Stage PD subjects from age-matched controls (FIG. 2a; Table 3).

Example 5

Specificity of Selected Biomarkers for Early-Stage PD

The specificity of the autoantibody biomarkers for Early-Stage PD was tested to determine if they could be used to successfully differentiate Early-Stage PD from other neurological and non-neurological diseases. To eliminate the possibility that the selected biomarkers were simply detecting non-specific CNS degeneration, the same Early-Stage PD serum samples were compared to samples from 50 patients with Alzheimer's disease (AD) and 30 samples from patients with multiple sclerosis (MS). Using the panel of 50 biomarkers, Early-Stage PD sera were readily distinguished from AD sera with an overall accuracy of 98.0% (sensitivity=98.1%; specificity=98.0%) (Table 2). ROC curve analysis yielded an AUC of 0.99 and comparable values for sensitivity and specificity (Table 3). Using the panel of only four biomarkers yielded an overall accuracy of 97.4% (ROC AUC=0.99; sensitivity=0.98; specificity=0.98) (Table 3). Similarly, both biomarker panels were able to readily distinguish Early-Stage PD from MS subjects with comparable overall accuracy (Tables 2 and 3).

Assays were also carried out to determine the specificity of the Early-Stage PD diagnostic biomarkers in the face of non-neurological disease, in this case breast cancer. Results showed that 30 breast cancer (BC) samples were successfully differentiated from the 103 Early-Stage PD samples with an overall accuracy of 97.7% (sensitivity=98.1%; specificity=96.7%; ROC AUC=0.99) for the full panel of 50 biomarkers (Table 3). ROC analysis using the panel of four biomarkers yielded an AUC of 0.99, a sensitivity of 0.98, and a specificity of 0.97 (Table 3). These results demonstrate that the diagnostic panels of 50 and four autoantibody biomarkers were comparably accurate in differentiating Early-Stage PD from both neurological and non-neurological controls.

Example 6

Use of Selected Panels of PD Biomarkers to Stage PD Progression

In this example, assays were carried out to examine whether the selected panels of 50 and four Early-Stage PD autoantibody biomarkers could distinguish Early-Stage PD from later stages with more advanced pathology.

Figure 2B:
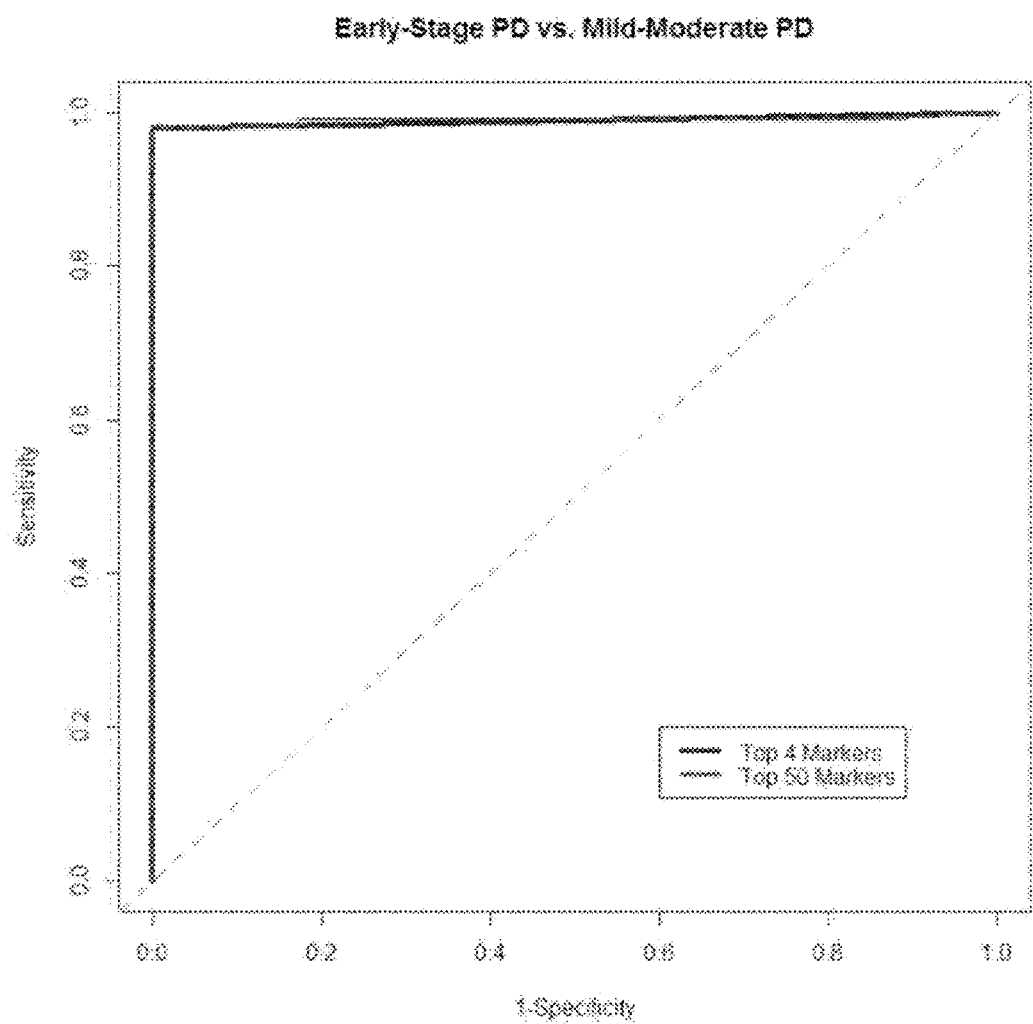

To address this, 103 Early-Stage PD serum samples were compared to 29 mild/moderate-stage PD samples using RF. Early-Stage PD samples were correctly classified with an overall accuracy of 98.5% and an OOB error of 1.5% (sensitivity=98.1%; specificity=100.0%) (Table 2) and a ROC AUC of 0.98 (FIG. 2b; Table 3) using the panel of 50 biomarkers. Comparable results were obtained with the panel of four Early-Stage PD autoantibody biomarkers (FIG. 2b; Table 3). These findings highlight the high level of specificity of these biomarker panels for the diagnosis of Early-Stage PD, and also demonstrate the potential utility of separate and specific autoantibody biomarker panels for identifying discrete stages of PD disease progression, as illustrated in FIG. 3.

Example 7

Effects of Addition of Younger Controls on Biomarker Selection and Diagnostic Accuracy There is a growing realization that most CNS diseases are preceded by long prodromal phases of ongoing, gradually escalating pathology for many years prior to the emergence of detectable symptoms (Montine et al. Toxicologic pathology 39, 99-102 (2011), Gaig et al. Movement disorders: Official journal of the Movement Disorder Society 24 Suppl 2, S656-664 (2009), Tolosa et al. Journal of the neurological sciences 310, 4-8 (2011), and Berendse et al. Journal of the neurological sciences 310, 21-24 (2011)).

This reality makes it very difficult for samples derived from the aging population to be both age-matched and unequivocally pathology-free. To investigate the impact of this potential limitation, the effects of including younger, non-age-matched controls on the initial selection of Early-Stage PD autoantibody biomarkers were tested. To accomplish this, 52 Early-Stage PD samples were compared to a control group composed of 56 age-matched and 45 additional younger, non-age-matched controls. As described above, the top 50 Early-Stage PD autoantibody biomarkers were selected in Prospector on the basis of prevalence difference between the two groups. The utility of these 50 new biomarkers for distinguishing Early-Stage PD (n=103) subjects from age-matched controls (n=111) was then verified using RF, yielding an overall diagnostic accuracy of 88.8%, a sensitivity of 93.2% and specificity of 84.7%. When all Early-Stage PD samples (n=103) were compared to all age-matched and non-age-matched controls (n=156) these biomarkers yielded an overall diagnostic accuracy of 90.4%, a sensitivity of 94.2%, and a specificity of 87.8%. These results were comparable to those obtained using the original 50 biomarkers described above. This is not surprising considering that, among the 50 new early-PD biomarkers, 32 were found to overlap with the previous set of 50 biomarkers that were derived from inclusion of only age- and sex-matched controls, and the identities of the four top biomarkers remained unchanged (FIG. 5).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

EQUIVALENTS

One of ordinary skill in the art will recognize that there are many equivalents of the specific embodiments disclosed herein, and that those equivalents will require no more than routine experimentation in the art. Therefore, those equivalents must be considered part of this invention and as such must be considered to be covered by the following claims.

All references and citations disclosed herein are to be considered incorporated by reference in their entirety.

What is claimed is:

1. A system for optimizing treatment of Early Stage Parkinson's Disease in a subject in need, the system comprising:
   (a) a microarray comprising a substrate and target antigens immobilized onto the substrate, wherein the only target antigens immobilized onto the substrate are:
      (i) each of the following: tRNA pseudouridine synthase-like 1 (PUSL1), serine/threonine-protein kinase MARK1, interleukin-20 (IL20), and C-C motif chemokine 19 (CCL19); and
      (ii) at least one additional antigen selected from the group consisting of T-cell leukemia/lymphoma protein 1B (TCL1B), Serine/threonine-protein kinase PLK1 (PLK1), Transcription factor 19 (TCF19), Uncharacterized protein C11orf52 (C11orf72), Arf-GAP with dual PH domain-containing protein 2 (ADAP2), Alpha-tubulin N-acetyltransferase 1 (ATAT1), NAD-dependent protein deacylase sirtuin-5, mitochondrial (SIRT5), Serine/threonine protein kinase BRSK1, MOB kinase activator 3C (MOB3C), RNA pseudouridylate synthase domain-containing protein 2 (RPUSD2), Fanconi anemia group M protein (FANCM), Lysine-specific demethylase 4D (KDM4D), Cytochrome c oxidase subunit A2 (COX6A2), Acyl-coenzyme A thioesterase 8 (ACOT8), U11/U12 small nuclear ribonucleoprotein 35 kDa protein (SNRNP35), ATP synthase subunit O (ATP5O), Peptidyl-tRNA hydrolase (ICT1), Homo sapiens zinc finger, C3HC-type containing 1 (ZC3HC1), Wilms tumor upstream neighbor 1 (WT1-AS), hypothetical protein LOC150577 (LOC150577), Translational activator of cytochrome c oxidase 1 (TACO1), Zinc finger protein 808 (ZNF808), Bifunctional 3'-phosphoadenosine 5'-phosphosulfate synthase 2 (PAPSS2), 60S ribosome subunit biogenesis protein (NIP7), Regulator of G-protein signaling 13 (RGS13), Homo sapiens hypothetical protein LOC147646 (LOC147646), Homo sapiens hypothetical LOC388528 (LOC388528), Homo sapiens hypothetical LOC150371 (LOC150371), Putative chondrosarcoma-associated gene 1 protein (CSAG1), cDNA clone BC103660, AP/microtubule affinity-regulating kinase 4, Mesoderm-specific transcript homolog protein (MEST), Human cDNA ORF Clone (C11orf72), Macaca fascicularis brain cDNA clone (QorA-12280), Macaca fascicularis brain cDNA clone (QorA-10370), 40S ribosomal protein S18 (RPS18), Putative E3 ubiquitin-protein ligase UNKL (UNKL), Protein BUD31 homolog (BUD31), Homo sapiens hypothetical LOC400763 (LOC400763), HCG1986256, Homo sapiens hypothetical LOC400027 (LOC400027), Homo sapiens homeobox B5 (HOXB5), Tubulin polyglutamylase TTLL1, 39S ribosomal protein L19, mitochondrial (MRPL19), MAP kinase-activated protein kinase 5 (MAPKAPK5), and Exosome complex component RRP40 (EXOSC3), or any antigenic fragment thereof;
   wherein the target antigens are attached to the microarray in a manner to allow for formation of an immunocomplex of each immobilized target antigen with its corresponding autoantibody upon contact with a biological sample from the subject containing the corresponding autoantibody;
   (b) a detecting agent to allow for identification for formation of the immunocomplex between each immobilized target antigen and its corresponding autoantibody; and
   (c) a computing system having a target antigen database and software algorithm stored in a non-transitory computer readable medium, the computing system configured to generate a report identifying the risk of a subject in developing Early Stage Parkinson's Disease, wherein formation of immunocomplexes of the target antigens with corresponding autoantibodies indicates the subject as being at risk of developing Early-Stage Parkinson's Disease, and
   wherein the system provides for a treatment plan for Early-Stage Parkinson's Disease.

2. The system of claim 1, wherein the treatment plan includes at least one low dose anti-Parkinson's agent selected from the group consisting of antioxidants, levodopa preparations, carbidopa preparations, MAO inhibitors, anticholinergics, COMT inhibitors, and any combinations thereof.

3. The system of claim 1, wherein the biological sample is at least one selected from the group consisting of serum, plasma, whole blood, CSF, saliva, and sputum.

4. The system of claim 1, wherein the at least one additional target antigens comprises at least two antigens selected from the group consisting of TCL1B, PLK1, TCF19, C11orf72, ADAP2, ATAT1, SIRT5, BRSK1, MOB3C, RPUSD2, FANCM, KDM4D, COX6A2, ACOT8, SNRNP35, ATP5O, ICT1, ZC3HC1, WT1-AS, LOC150577, TACO1, ZNF808, PAPSS2, NIP7, RGS13, LOC147646, LOC388528, LOC150371, CSAG1, cDNA clone BC103660, MAP/microtubule affinity-regulating kinase 4, MEST, C11orf72, QorA-12280, QorA-10370, RPS18, UNKL, BUD31, LOC400763, HCG1986256, LOC400027, HOXB5, TTLL1, MRPL19, MAPKAPK5, and EXOSC3.

5. The system of claim 1, wherein the at least one additional antigen comprises at least three antigens selected from the group consisting of TCL1B, PLK1, TCF19, C11orf72, ADAP2, ATAT1, SIRT5, BRSK1, MOB3C, RPUSD2, FANCM, KDM4D, COX6A2, ACOT8, SNRNP35, ATP5O, ICT1, ZC3HC1, WT1-AS, LOC150577, TACO1, ZNF808, PAPSS2, NIP7, RGS13, LOC147646, LOC388528, LOC150371, CSAG1, cDNA clone BC103660, MAP/microtubule affinity-regulating kinase 4, MEST, C11orf72, QorA-12280, QorA-10370, RPS18, UNKL, BUD31, LOC400763, HCG1986256, LOC400027, HOXB5, TTLL1, MRPL19, MAPKAPK5, and EXOSC3.

6. The system of claim 1, wherein the at least one additional antigen comprises at least four antigens selected from the group consisting of TCL1B, PLK1, TCF19, C11orf72, ADAP2, ATAT1, SIRT5, BRSK1, MOB3C, RPUSD2, FANCM, KDM4D, COX6A2, ACOT8, SNRNP35, ATP5O, ICT1, ZC3HC1, WT1-AS, LOC150577, TACO1, ZNF808, PAPSS2, NIP7, RGS13, LOC147646, LOC388528, LOC150371, CSAG1, cDNA clone BC103660, MAP/microtubule affinity-regulating kinase 4, MEST, C11orf72, QorA-12280, QorA-10370, RPS18, UNKL, BUD31, LOC400763, HCG1986256, LOC400027, HOXB5, TTLL1, MRPL19, MAPKAPK5, and EXOSC3.

7. The system of claim 1, wherein the detecting agent comprises a secondary antibody.

8. A system for optimizing treatment of Early Stage Parkinson's Disease in a subject in need, the system comprising:
   (a) a microarray comprising a substrate and target antigens immobilized onto the substrate, wherein the only target antigens immobilized onto the substrate are the following: tRNA pseudouridine synthase-like 1

(PUSL1), serine/threonine-protein kinase MARK1, interleukin-20 (IL20), and C-C motif chemokine 19 (CCL19);
wherein the target antigens are attached to the microarray in a manner to allow for formation of an immunocomplex of each immobilized target antigen with its corresponding autoantibody upon contact with a biological sample from the subject containing the corresponding autoantibody;
(b) a detecting agent to allow for identification for formation of the immunocomplex between each immobilized target antigen and its corresponding autoantibody; and
(c) a computing system having a target antigen database and software algorithm stored in a non-transitory computer readable medium, the computing system configured to generate a report identifying the risk of a subject in developing Early Stage Parkinson's Disease, wherein formation of immunocomplexes of the target antigens with corresponding autoantibodies indicates the subject as being at risk of developing Early-Stage Parkinson's Disease, and
wherein the system provides for a treatment plan for Early-Stage Parkinson's Disease.

9. The system of claim 8, wherein the treatment plan includes at least one low dose anti-Parkinson's agent selected from the group consisting of antioxidants, levodopa preparations, carbidopa preparations, MAO inhibitors, anticholinergics, COMT inhibitors, and any combinations thereof.

10. The system of claim 8, wherein the biological sample is at least one selected from the group consisting of serum, plasma, whole blood, CSF, saliva, and sputum.

11. The system of claim 8, wherein the detecting agent comprises a secondary antibody.

* * * * *

SEQUENCE LISTING

```
<160> NUMBER OF SEQ ID NOS: 7

<210> SEQ ID NO 1
<211> LENGTH: 5336
<212> TYPE: DNA
<213> ORGANISM: Homo sapiens

<400> SEQUENCE: 1
gctgctccgc gcgcagccgg ctcgggccgc tcctcctgac tgaggcgcgg cggcggcggt        60
ggctgtgacc gcgcggaccg agccgagaca ttcgcgccgg gggatcgggc gccgccgccg       120
ctgggccccg ggcgcgtgga tgcggctggg tcgggcggcg ccgtacacct gaggcggaga       180
acggggcgcg gcgcgggtga cgctgtcagg gccgcggttc ctgacgccca ggcgctcgcc       240
aggacgagcc aggcagtgat ttgaggcacc ggcttcacct tcacccatgg tccggagagc       300
ctagcggggc tcgccaccgc ctcccggctc cccttccacg cctcatcctg ccagcctcgc       360
cgccccgcca gcgccgggca accgcctcgc ccgaagcccct ccctcgttac tgtccgcata      420
ccccggcggc gccgccgcgg gaagcggctc cccctcctct tcctccgcgt cctcttccct       480
ctttcccccg ccggggccgc ttgttgcacc gccccgcggc ctgcgggagc cgctcgcccc       540
ggccttgtgc tcgcgtccgc accccttttcc tgtcgccccc cggggcccgc accacagccc     600
ggccggcgag accccggcca gacccccgctg cccgcacaaa atgtcggccc ggacgccatt     660
gccgacggtg aacgagcggg acacggaaaa tcatacatct gtggatggat atactgaacc     720
acacatccaa cctaccaagt cgagtagcag acagaacatc ccccggtgta gaaactccat      780
tacgtcagca acagatgaac agcctcacat tggaaattac cgtttacaaa aaacaatagg     840
gaagggaaat tttgccaaag tcaaattggc aagacacgtt ctaactggta gagaggttgc      900
tgtgaaaata atagacaaaa ctcagctaaa tcctaccagt ctacaaaagt tatttcgaga      960
agtacgaata atgaagatac tgaatcatcc taatatagta aaattgtttg aagttattga     1020
aacagagaag actctctatt tagtcatgga atacgcgagt gggggtgaag tatttgatta     1080
cttagttgcc catggaagaa tgaaagagaa agaggcccgt gcaaaattta ggcagattgt     1140
atctgctgta cagtattgtc atcaaaagta cattgttcac cgtgatctta aggctgaaaa     1200
ccttctcctt gatggtgata tgaatattaa aattgctgac tttggttta gtaatgaatt      1260 tacagttggg aacaaattgg acacattttg tggaagccca ccctatgctg ctcccgagct     1320
tttccaagga aagaagtatg atgggcctga agtggatgtg tggagtctgg gcgtcattct     1380
```

```
ctatacatta gtcagtggct ccttgccttt cgatggccag aatttaaagg aactgcgaga   1440
gcgagtttta cgagggaagt accgtattcc cttctatatg tccacagact gtgaaaatct   1500
tctgaagaaa ttattagtcc tgaatccaat aaagagaggc agcttggaac aaataatgaa   1560
agatcgatgg atgaatgttg gtcatgaaga ggaagaacta agccatata ctgagcctga    1620 tccggatttc aatgacacaa aaagaataga cattatggtc accatgggct tgcacgaga    1680 tgaaataaat gatgccttaa taaatcagaa gtatgatgaa gttatggcta cttatattct   1740
tctaggtaga aaaccacctg aatttgaagg tggtgaatcg ttatccagtg gaaacttgtg   1800
tcagaggtcc cggcccagta gtgacttaaa caacagcact cttcagtccc ctgctcacct   1860
gaaggtccag agaagtatct cagcaaatca gaagcagcgg cgtttcagtg atcatgctgg   1920
tccatccatt cctcctgctg tatcatatac caaaagacct caggctaaca gtgtggaaag   1980
tgaacagaaa gaggagtggg acaaagatgt ggctcgaaaa cttggcagca caacagttgg   2040
atcaaaaagc gagatgactg caagccctct tgtagggcca gagaggaaaa aatcttcaac   2100
tattccaagt aacaatgtgt attctggagg tagcatggca agaaggaata catatgtctg   2160
tgaaaggacc acagatcgat acgtagcatt gcagaatgga aaagacagca gccttacgga   2220
gatgtctgtg agtagcatat cttctgcagg ctcttctgtg gcctctgctg tcccctcagc   2280
acgaccccgc caccagaagt ccatgtccac ttctggtcat cctattaaag tcacactgcc   2340
aaccattaaa gacggctctg aagcttaccg gcctggtaca acccagagag tgcctgctgc   2400
ttccccatct gctcacagta ttagtactgc gactccagac cggacccgtt tccccgagg    2460 gagctcaagc cgaagcactt tccatggtga acagctccgg gagcgacgca gcgttgctta   2520
taatgggcca cctgcttcac catcccatga acgggtgca tttgcacatg ccagaagggg    2580
aacgtcaact ggtataataa gcaaaatcac atccaaattt gttcgcaggg atccaagtga   2640
aggcgaagcc agtggcagaa ccgacacctc aagaagtaca tcaggggaac caaaagaaag   2700
agacaaggaa gagggtaaag attctaagcc gcgttctttg cggttcacat ggagtatgaa   2760
gaccactagt tcaatggacc ctaatgacat gatgagagaa atccgaaaag tgttagatgc   2820
aaataactgt gattatgagc aaaaagagag attttttgctt ttctgtgtcc atggagacgc   2880
tagacaggat agcctcgtgc agtgggagat ggaagtctgc aagttgccac gactgtcact   2940
taatggggtt cgcttcaagc gaatatctgg gacatctatt gcctttaaga acattgcatc   3000
aaaaatagca aatgagctta agctgtaaag aagtccaaat ttacaggttc agggaagata   3060
catacatata tgaggtacag ttttttgaatg tactggtaat gcctaatgtg gtctgcctgt   3120
gaatctcccc atgtagaatt tgcccttaat gcaataaggt tatacatagt tatgaactgt   3180
aaaattaaag tcagtatgaa ctataataaa tatctgtagc ttaaaaagta ggttcacatg   3240
tacaggtaag tatattgtgt atttctgttc attttctgtt catagagttg tataataaaa   3300
catgattgct taaaaacttg tatagttgtc tagatttctg cacctgaatg tatgtttgat   3360
gctttgattt gaaaatgttc ttccctgtta tttacattct ggtgggtttt taaaattctt   3420
acctccatca tgcaatttg aaaattgtgt ccagaattaa aagtgcatag aaatagcctt    3480
tacaattgta gcatggacct ttaaaaattg ttttaaaatc ttatttaaat ttaaaccaga   3540
agctgaaaaa tagatcagct ttattataca caaaattatt actgcttatc tttgctcttt   3600
tccttgttat cccgcaaggt ttagttgaga agatacaaaa tgtttacagt gttggcactt   3660
agagttttta aattcaagta catgaaattc agtaatagca ttgccttgag ctaactagga   3720
```

```
agtaccggga aaaaagttaa atctacatca gtttcttttt gaactttgaa gtgttttctg    3780
acccactgct aactgtagca acaaaattta aagaaaaaaa aacatacttt atctggctat    3840
tataacataa actgtcacgt aggtttgctg ccttcagaat accgcaattt aattgcggga    3900
atataataat attgggactg tttcacagca caaactcatc tttacagtgt tgatcaatgc    3960
atcagttaag aaataatgcc acctcaggaa ttaactggca ttgggaacat ttgcctcatt    4020
ctcctgctat cctcttcatt caccccctgcc actgtaatat ctataagtac ttaagagact    4080
tgtgagcaaa acatactatt tataacagta tatgattgat ttatgcttat gtggttgttc    4140
agtttgttcc catgtaactc gtttgtttta aatattttgc cagatttctt gtatttattc    4200
cacatcatta tgcctataat gtgccgcttt gtgattgggc atttgcctac ttttctttca    4260
taattagtga tatatgcgat gtaaaaccac tagtaaaggt acattttaat acttgttatt    4320
ttatactgaa ttagccttgg aggttgactg tgcaatgtta tttactgttg taattactgt    4380
aataccaaca tatgggcccc atctgcacac tcctgaaaaa cagaaagtgt attcaaattt    4440
tatcagttta agaaaataaa agctgtgata atactgtaaa ttccaaccta cattagaagg    4500
tctaagtgta ggtgatgtgc cattccataa tggcttccag actagggtga attttatgtt    4560
ctgtactgta ctgtgatgta gctttcttct gtaacagtta tgttttaaaa ttaagtgagt    4620
tttttttttg ccttagcaaa gggtggtgtt tgaaaaaaaa aatgtgtagc ccctttttaa    4680
cctagtgttc attcaaaaaa aaattgatgc aaatctttat tcactttcac tggtgcacac    4740 tgaaattta cttgaacagt tctcataata aagcacttgt cttttgctct ttatcagaat     4800
gtgaattacc tgttttctgg tacaaaagta ttctgtatga ggagtttatt gtatgtgttc    4860
taaatttagt tggcaaaggg tgaagctgtg aaggttttca agattattga aactatgaag    4920
gtttcttgtc attatgacaa gaaagtttaa tcttttttata ggaattcctg tcactgaaat   4980 acgttttaa aaaaatagac tcatgtgttt tccacggtag aaactgatat ttttttacat     5040
tttctcactg tggccaactc ttctgtgttt gtagaaagga atttgacttc aatatctttt    5100
atgaactaaa aatgaaatct tgatactcac tttagatttt tcattttatg tgttcatgac    5160
aacataaata tttttcaaag atttagagga attttgcaat gtgtttgcat aaataaatac    5220
cagtttatgt tcaccggcta tgtgatacca ggatttcctt ggcttctgtt gaaatattat    5280
ttgatatgac atcccttata ttaaattaat tatttttgtaa aaaaaaaaaa aaaaaa      5336
```

<210> SEQ ID NO 2
<211> LENGTH: 795
<212> TYPE: PRT
<213> ORGANISM: Homo sapiens

<400> SEQUENCE: 2

```
Met Ser Ala Arg Thr Pro Leu Pro Thr Val Asn Glu Arg Asp Thr Glu
1               5                   10                  15

Asn His Thr Ser Val Asp Gly Tyr Thr Glu Pro His Ile Gln Pro Thr
            20                  25                  30

Lys Ser Ser Arg Gln Asn Ile Pro Arg Cys Arg Asn Ser Ile Thr
        35                  40                  45

Ser Ala Thr Asp Glu Gln Pro His Ile Gly Asn Tyr Arg Leu Gln Lys
    50                  55                  60

Thr Ile Gly Lys Gly Asn Phe Ala Lys Val Lys Leu Ala Arg His Val
65                  70                  75                  80

Leu Thr Gly Arg Glu Val Ala Val Lys Ile Ile Asp Lys Thr Gln Leu
                85                  90                  95
```

```
Asn Pro Thr Ser Leu Gln Lys Leu Phe Arg Glu Val Arg Ile Met Lys
            100                 105                 110

Ile Leu Asn His Pro Asn Ile Val Lys Leu Phe Glu Val Ile Glu Thr
            115                 120                 125

Glu Lys Thr Leu Tyr Leu Val Met Glu Tyr Ala Ser Gly Gly Glu Val
            130                 135                 140

Phe Asp Tyr Leu Val Ala His Gly Arg Met Lys Glu Lys Glu Ala Arg
145                 150                 155                 160

Ala Lys Phe Arg Gln Ile Val Ser Ala Val Gln Tyr Cys His Gln Lys
                165                 170                 175

Tyr Ile Val His Arg Asp Leu Lys Ala Glu Asn Leu Leu Leu Asp Gly
            180                 185                 190

Asp Met Asn Ile Lys Ile Ala Asp Phe Gly Phe Ser Asn Glu Phe Thr
            195                 200                 205

Val Gly Asn Lys Leu Asp Thr Phe Cys Gly Ser Pro Pro Tyr Ala Ala
            210                 215                 220

Pro Glu Leu Phe Gln Gly Lys Lys Tyr Asp Gly Pro Glu Val Asp Val
225                 230                 235                 240

Trp Ser Leu Gly Val Ile Leu Tyr Thr Leu Val Ser Gly Ser Leu Pro
                245                 250                 255

Phe Asp Gly Gln Asn Leu Lys Glu Leu Arg Glu Arg Val Leu Arg Gly
            260                 265                 270

Lys Tyr Arg Ile Pro Phe Tyr Met Ser Thr Asp Cys Glu Asn Leu Leu
            275                 280                 285

Lys Lys Leu Leu Val Leu Asn Pro Ile Lys Arg Gly Ser Leu Glu Gln
            290                 295                 300

Ile Met Lys Asp Arg Trp Met Asn Val Gly His Glu Glu Glu Glu Leu
305                 310                 315                 320

Lys Pro Tyr Thr Glu Pro Asp Pro Asp Phe Asn Asp Thr Lys Arg Ile
                325                 330                 335

Asp Ile Met Val Thr Met Gly Phe Ala Arg Asp Glu Ile Asn Asp Ala
            340                 345                 350

Leu Ile Asn Gln Lys Tyr Asp Glu Val Met Ala Thr Tyr Ile Leu Leu
            355                 360                 365

Gly Arg Lys Pro Pro Glu Phe Glu Gly Gly Glu Ser Leu Ser Ser Gly
            370                 375                 380

Asn Leu Cys Gln Arg Ser Arg Pro Ser Ser Asp Leu Asn Asn Ser Thr
385                 390                 395                 400

Leu Gln Ser Pro Ala His Leu Lys Val Gln Arg Ser Ile Ser Ala Asn
                405                 410                 415

Gln Lys Gln Arg Arg Phe Ser Asp His Ala Gly Pro Ser Ile Pro Pro
            420                 425                 430

Ala Val Ser Tyr Thr Lys Arg Pro Gln Ala Asn Ser Val Glu Ser Glu
            435                 440                 445

Gln Lys Glu Glu Trp Asp Lys Asp Val Ala Arg Lys Leu Gly Ser Thr
            450                 455                 460

Thr Val Gly Ser Lys Ser Glu Met Thr Ala Ser Pro Leu Val Gly Pro
465                 470                 475                 480

Glu Arg Lys Lys Ser Ser Thr Ile Pro Ser Asn Asn Val Tyr Ser Gly
                485                 490                 495

Gly Ser Met Ala Arg Arg Asn Thr Tyr Val Cys Glu Arg Thr Thr Asp
            500                 505                 510
```

Arg Tyr Val Ala Leu Gln Asn Gly Lys Asp Ser Ser Leu Thr Glu Met
        515                 520                 525

Ser Val Ser Ser Ile Ser Ser Ala Gly Ser Ser Val Ala Ser Ala Val
    530                 535                 540

Pro Ser Ala Arg Pro Arg His Gln Lys Ser Met Ser Thr Ser Gly His
545                 550                 555                 560

Pro Ile Lys Val Thr Leu Pro Thr Ile Lys Asp Gly Ser Glu Ala Tyr
                565                 570                 575

Arg Pro Gly Thr Thr Gln Arg Val Pro Ala Ala Ser Pro Ser Ala His
            580                 585                 590

Ser Ile Ser Thr Ala Thr Pro Asp Arg Thr Arg Phe Pro Arg Gly Ser
        595                 600                 605

Ser Ser Arg Ser Thr Phe His Gly Glu Gln Leu Arg Glu Arg Arg Ser
    610                 615                 620

Val Ala Tyr Asn Gly Pro Pro Ala Ser Pro Ser His Glu Thr Gly Ala
625                 630                 635                 640

Phe Ala His Ala Arg Arg Gly Thr Ser Thr Gly Ile Ile Ser Lys Ile
                645                 650                 655

Thr Ser Lys Phe Val Arg Arg Asp Pro Ser Glu Gly Glu Ala Ser Gly
            660                 665                 670

Arg Thr Asp Thr Ser Arg Ser Thr Ser Gly Glu Pro Lys Glu Arg Asp
        675                 680                 685

Lys Glu Gly Lys Asp Ser Lys Pro Arg Ser Leu Arg Phe Thr Trp
    690                 695                 700

Ser Met Lys Thr Thr Ser Ser Met Asp Pro Asn Asp Met Met Arg Glu
705                 710                 715                 720

Ile Arg Lys Val Leu Asp Ala Asn Asn Cys Asp Tyr Glu Gln Lys Glu
                725                 730                 735

Arg Phe Leu Leu Phe Cys Val His Gly Asp Ala Arg Gln Asp Ser Leu
            740                 745                 750

Val Gln Trp Glu Met Glu Val Cys Lys Leu Pro Arg Leu Ser Leu Asn
        755                 760                 765

Gly Val Arg Phe Lys Arg Ile Ser Gly Thr Ser Ile Ala Phe Lys Asn
    770                 775                 780

Ile Ala Ser Lys Ile Ala Asn Glu Leu Lys Leu
785                 790                 795

<210> SEQ ID NO 3
<211> LENGTH: 1262
<212> TYPE: DNA
<213> ORGANISM: Homo sapiens

<400> SEQUENCE: 3
cgcctctgac gccaccggct gggctccgcc atgagttcgg cgccggcctc aggctccgtg      60
cgcgcgcgct atcttgtgta cttccagtac gtgggcaccg actttaacgg ggtcgcggcc     120
gtcaggggca ctcagcgcgc cgtcggggtc cagaactacc tggaggaggc cgccgagcgg     180
ctgaattccg tggagccggt caggttcacc atctccagcc gcacggacgc cggggtccac     240
gccctgagca cgcggcgcca cctggacgtc agcgccgct caggccggcc gcccttcccg     300
cccgaggtcc tggccgaggc cctcaacaca cacctgcggc acccggccat cagggtcctg     360
cgggccttcc gagtgcccag cgacttccac gctcgtcacg cagccacgtc ccggacctac     420
ctgtaccgcc tggccactgg ctgtcaccgg cgtgatgagc tgccggtgtt tgaacgcaac     480
ctatgctgga ctctcccggc agactgcctg gatatggtcg ccatgcagga agccgcccag     540

```
cacctcctcg gcacacacga cttcagcgcc ttccagtccg ctggcagccc ggtgccgagc    600
cccgtgcgaa cgctgcgccg ggtctccgtt tccccaggcc aagccagccc cttggtcacc    660
cccgaggaga gcaggaagct gcggttctgg aacctggagt ttgagagcca gtctttcctg    720
tatagacagg tacggaggat gacggctgtg ctggtggccg tggggctggg ggctttggca    780
cctgcccagg tgaagacgat tctggagagc caagatcccc tgggcaagca ccagacacgt    840
gtagccccag cccacggctt attcctcaag tcagtgctgt acgggaacct cggtgctgcc    900
tcctgcaccc tgcaggggcc acagttcggg agccacggat gaccctggac actcaagcca    960
aagttaggcc acaccaggcc caaccctgtg ctggtcaagc cagggcagtc acagctgctt   1020
ggggcccaca gcactgctgc ctggtctcca cagtagcctc cctgcccggg tcccagcacc   1080
ctggatgccc gtctctgtcc caggcgggat ggggcacagt gcaggacaca gccatgtaca   1140
ccaagaagag agtaccaagt agtctttgt tcagctttta ctggaaactg ctgtctagga    1200
ccacctgccc taaccaggaa taaaggcaag acagcctgga aaaaaaaaa aaaaaaaaa     1260 aa                                                                    1262
```

<210> SEQ ID NO 4
<211> LENGTH: 303
<212> TYPE: PRT
<213> ORGANISM: Homo sapiens

<400> SEQUENCE: 4

```
Met Ser Ser Ala Pro Ala Ser Gly Ser Val Arg Ala Arg Tyr Leu Val
1               5                   10                  15

Tyr Phe Gln Tyr Val Gly Thr Asp Phe Asn Gly Val Ala Ala Val Arg
            20                  25                  30

Gly Thr Gln Arg Ala Val Gly Val Gln Asn Tyr Leu Glu Glu Ala Ala
        35                  40                  45

Glu Arg Leu Asn Ser Val Glu Pro Val Arg Phe Thr Ile Ser Ser Arg
    50                  55                  60

Thr Asp Ala Gly Val His Ala Leu Ser Asn Ala Ala His Leu Asp Val
65                  70                  75                  80

Gln Arg Arg Ser Gly Arg Pro Pro Phe Pro Pro Glu Val Leu Ala Glu
                85                  90                  95

Ala Leu Asn Thr His Leu Arg His Pro Ala Ile Arg Val Leu Arg Ala
            100                 105                 110

Phe Arg Val Pro Ser Asp Phe His Ala Arg His Ala Ala Thr Ser Arg
        115                 120                 125

Thr Tyr Leu Tyr Arg Leu Ala Thr Gly Cys His Arg Arg Asp Glu Leu
    130                 135                 140

Pro Val Phe Glu Arg Asn Leu Cys Trp Thr Leu Pro Ala Asp Cys Leu
145                 150                 155                 160

Asp Met Val Ala Met Gln Glu Ala Ala Gln His Leu Leu Gly Thr His
                165                 170                 175

Asp Phe Ser Ala Phe Gln Ser Ala Gly Ser Pro Val Pro Ser Pro Val
            180                 185                 190

Arg Thr Leu Arg Arg Val Ser Val Ser Pro Gly Gln Ala Ser Pro Leu
        195                 200                 205

Val Thr Pro Glu Glu Ser Arg Lys Leu Arg Phe Trp Asn Leu Glu Phe
    210                 215                 220

Glu Ser Gln Ser Phe Leu Tyr Arg Gln Val Arg Arg Met Thr Ala Val
225                 230                 235                 240
```

```
Leu Val Ala Val Gly Leu Gly Ala Leu Ala Pro Ala Gln Val Lys Thr
            245                 250                 255

Ile Leu Glu Ser Gln Asp Pro Leu Gly Lys His Gln Thr Arg Val Ala
        260                 265                 270

Pro Ala His Gly Leu Phe Leu Lys Ser Val Leu Tyr Gly Asn Leu Gly
    275                 280                 285

Ala Ala Ser Cys Thr Leu Gln Gly Pro Gln Phe Gly Ser His Gly
    290                 295                 300

<210> SEQ ID NO 5
<211> LENGTH: 6634
<212> TYPE: DNA
<213> ORGANISM: Homo sapiens

<400> SEQUENCE: 5
taaataatgg gaagcctttc aacttgaaac aggctcctag gagaccagaa gcagcagcct      60
ttcctgagct caggtaagag atcttaccct ctactgacac tgctcacgtt gttgtgagga    120
tcacctactt ctcctaatca tttacccagg tatgttcaag gtcacatcta aaggacccct    180
ttccacgagg acaaaatctc tttgaggaca ataatcatc atgtttatct ttgtacttca    240
gtacctagca caacattcaa gacagcgggt gctcattaaa tgctcatcaa attgttagtt    300
caggacaact aacatcaatc tctacttaaa atgaattgat cacttgctct gtgctaagtg    360
tataaatcat agattattgt atttaaataa tcgatttaaa atcaaaacaa tttctgggtt    420
aagtttaatt atcaccattt tggggttaag aaaattaaac tcagaggtga gttgacttgt    480
ccaaggtcac atagaggtag ggtggccaac tcattccagt ttacctgtgg ttttttccagt   540 tttaaaactg aaattttcgt atttcaggaa ccattcctg cccccaacc tcagtcctgg      600 gtaaactgga atgacccaca tcaatggaaa ctagtaaagc gaggatttat ttggacccag    660
ttctcttgtc tccaaaccca gagtcctctt tgattctttt gggtttggtt tgctttttc     720 cttttcctac atttgacagt atctcgagtg gtcacaaatg taaaaaatgt ctagcatatt    780
gcctggcata taggaaaaat tcagtaagtg ataatgatta tcagtgctgt gccaagctat    840
ggagccagcc atatatatat ggatgtgtgc atatatatat atgatgtgtg tgtatatata    900
tatgtcttta taaatttat gtatttattt cttctaaaaa tattaaagta tttgagaaaa     960
ttgaaaaatt aaaaagtagg tttattacga ctcatgactt taagttttaaa tattttattt  1020 ctgccccaaa caaatttat tataatttta ctgtcctggt tttaagggaa ggaaactcat    1080
caataatatt ttcatcatat gcttttgaga aacaaagtta accattaaga atgaaacatg   1140
aaaacatgtg aatagtggta caaattttc cttttgcttc aatatggctc agcatggcac    1200
tgtcgaattt tgtctttata taaattttg atattttgtt tgtcataagc ttttaattc      1260 atttttatat tgcactaaaa tattttatc ttgatgactg aggttttta gtgctccctt     1320 aaattttgca cctaaaatga gtgcctcaat tgttttaccc taacctcagc ccattattat   1380
tttatcttaa aactcagcaa acaccctaac ctgctctctt actgaggagg ctcgcccaag   1440
aataaatgag ttccgtcatt gcctttcttc tctgactttt gggaccattt gcttggtcta   1500
ggacctgagt tgcaggtcca ggaaagcgtg tactctcgaa tccacccagg agtgcctgac   1560
tacagtcctc ctgcagaggg cgctgtggag tcccagacac gagtgttagg tggaatcggg   1620
ctgattgccc atcacgtctt gccttccct ggcagtaggc ttgttatgaa atcattgact    1680
ttctatttgc ctctggggct taagcgaatc tgttaccctc aaataaccta tctgatctca   1740
```

```
gacaaatgcc aaacagagct cagtttctct gccctgtggg tggccataaa atccagacaa    1800 tttccccta  ggtgttttcg atggcgcagc cacagcttct gtgagattcg atttctcccc    1860
agttcccctg tgggtctgag gggaccagaa gggtgagcta cgttggcttt ctggaagggg    1920
aggctatatg cgtcaattcc ccaaaacaag ttttgacatt tcccctgaaa tgtcattctc    1980
tatctattca ctgcaagtgc ctgctgttcc aggccttacc tgctgggcac taacggcgga    2040
gccaggatgg ggacagaata aaggagccac gacctgtgcc accaactcgc actcagactc    2100
tgaactcaga cctgaaatct tctcttcacg ggaggcttgg cagttttct tagtaagttg     2160 cgtggatggg ccacactgtc tgaggccaga taaggctgtt ctcttcccct gaccccccac    2220
ccctcacccc gtggacactt ggaggagggg aaactcagta agtcatgctc tcttctttga    2280
attcctagct cctgtggtct ccagatttca ggcctaagat gaaagcctct agtcttgcct    2340
tcagccttct ctctgctgcg ttttatctcc tatggactcc ttccactgga ctgaagacac    2400
tcaatttggg aagctgtgtg atcgccacaa accttcagga aatacgaaat ggattttctg    2460
agatacgggg cagtgtggta cgtaagcggg tatctacctc tcctgaaagc ctttctctt     2520 ccttccttgt ccgtttctct ttcctggcag tactggcagt gtaatcataa aaagaggcag    2580 gctgggatt  ccttacccgg gggatgtatt ccaaagaaat aactgtagtt caaatattta    2640
aaatgttttg ggaaaggaca cctcccacta gttcttggca gggagtggat gagaagtctt    2700
gatattgaag accctggcag caggcactga ctcatccttg cttgttttgt cttcttctgt    2760
ttagcaagcc aaagatggaa acattgacat cagaatctta aggaggactg agtctttgca    2820
agacacaaag gtatgtgctt ggcccagaca aactctggga ggaggagtgg agtgggagca    2880
tctccatcac cctggtcttg tctctgctct cccctttccc ctcaccaata tacctgtggt    2940
tttttgcagc ctgcgaatcg atgctgcctc ctgcgccatt tgctaagact ctatctggac    3000
agggtattta aaaactacca gacccctgac cattatactc tccggaagat cagcagcctc    3060
gccaattcct ttcttaccat caagaaggac ctccggctct gtgtgagtgt gggtcttggg    3120
tgacaggatg catctcagca cacagcttca atggcttagc aactaaactc tctttcctac    3180
ctccatttaa tggatggaga aactgagtcc aaaagttcta ataatctgtg ttgagacatg    3240
tgactaggta ataagaactc agttttattg acttttcggt atatgctcta ggcaaaaagt    3300
actttgcaaa gtctaaagaa ctataagatg ctaactattt gatattaatg ataactctgt    3360
tgtctttgaa attatacttt ttctgtaggt gaggtatcct acagtatatt agtgcgtcct    3420
ctgtctaggc agtcaattag tagaccattg agcttgacct cagaatatag tctgaatagg    3480
acctaggaat tcaattcttt tttttttttt tctcaatggg ggctcaaaga gctctgggat    3540
agagctccta gactacagct gggggttgtg gggaggccag atggggtacg gggatggcaa    3600
atgccttcag tactgcctgc ctatttctaa aaaagaagtg atgagttcca tgtttgagcc    3660
taaaaggtgg cttcctctcc tagctgatga tgaacttaat gattccaaat gtgaggtctg    3720
aaagagcttt tctataggaa taagcatcct cagggttgtg ggtgaaagag tagagtttct    3780
acctgcttca tgtcaatggc aaaaaatcag aatctgtaat ataatctatt attctttggg    3840 tcctttttcag catgcccaca tgacatgcca ttgtggggag gaagcaatga agaaatacag    3900
ccagattctg agtcactttg aaaaggtata tgcgactttg gcattgattg ggatgggtgt    3960 gtttttaagaa ctgagatcat aggtaggtgg gatggttatt cactgttaga catcctgtag   4020
ccttcaggtt catagccctc tgaaatcatg aggaccagcc cttgctttaa cccagggac    4080 acccatccag gctctagagg agtaccctct ctgggtgatg ctctggaaat ggaaagggaa    4140
```

```
tggccatgat tccatcaagt cactacagtg acatctggat cttttagctg cacaaaccag    4200
aggcaatagt tttacaatgt tcacacactt ctatgtacct tgaaaacac tcacaatttc     4260 acacacacac ccatgccatt caatttctca ccttcacacc ttctcatgtc tgccaggaag    4320
gcctggattt cactcctcac tgactaaatc ctactcatcc tttaaagact cagcctgggc    4380
atcactttca ggaaggtgct ggctccttct ctcagagtta gatgcctccc acatcatctt    4440
gtaggaattt catcccttta ttcaccacac tacattttag ttgcctgttt ttgccagtct    4500
cctcactcaa ctgtggatag ggattgtgcc attcacctttt tcatccctaa ccatcagcta   4560
ggtgattggc acaatcaata tctgttcaac tgatgtgtgc accgtaggca acccctacac    4620
acacacacag gcacgtgcac acacacacac acacgtttt cttaaagaaa atagcttgat     4680
tattttgatc tctgtgattc aagagtctta agtagcagtt ttacttctgc taccccttg     4740 cacctcagtt tctgtacata agaccagggt gatgaactca atgatttccc ttccttgtgt    4800
gatatcttga gattctataa cttctttaag tgcttcatct tgaaaagaat gctctgctta    4860
caattgtcag cagacctatc cataaaagag ataggtcctg gagcaaatgc tgtctcatga    4920
attgctaacc acatgggtgt gtgtctcttt cagctggaac ctcaggcagc agttgtgaag    4980
gctttggggg aactagacat tcttctgcaa tggatggagg agacagaata ggaggaaagt    5040
gatgctgctg ctaagaatat tcgaggtcaa gagctccagt cttcaatacc tgcagaggag    5100
gcatgacccc aaaccaccat ctctttactg tactagtctt gtgctggtca cagtgtatct    5160
tatttatgca ttacttgctt ccttgcatga ttgtctttat gcatcccaa tcttaattga     5220 gaccatactt gtataagatt tttgtaatat ctttctgcta ttggatatat ttattagtta    5280
atatatttat ttattttttg ctatttaatg tatttatttt tttacttgga catgaaactt    5340
taaaaaaatt cacagattat atttataacc tgactagagc aggtgatgta ttttatacaa    5400
gtaaaaaaaa aaaaccttgt aaattctaga agagtggcta gggggttat tcatttgtat    5460 tcaactaagg acatatttac tcatgctgat gctctgtgag atatttgaaaa ttgaaccaat   5520 gactacttag gatgggttgt ggaataagtt ttgatgtgga attgcacatc taccttacaa    5580
ttactgacca tccccagtag actccccagt cccataattg tgtatcttcc agccaggaat    5640
cctacacggc cagcatgtat ttctacaaat aaagttttct ttgcataaca tctgcttgga    5700
gtttgcaaat gtttcaagag cagagaccat gttgaggata agtttgaatc tcatttcacc    5760
ccaggtcctc ttgctccttt gaggaagaag atgtaggaac ctcgatcttc tctctcctgc    5820
agatttcatc ctcagctcta tctcctaatt catactgctc tgaccccacg actgccctcc    5880
tctcaaaagg actgtgacag agtgaggggc ttcagccatc tctgctttcg cctcattggc    5940
ttggagcact gccctttcta tacctctgtt ttctttctca ccccatacc ttgcaagaca     6000 aattacaatg ggcatgaggc gctattataa aggttaaaaa cacacaggtg caaagtgtag    6060
gtctagagtc ttgcccagac aggtgtatga gccccctttt gaggcccttc cattttggat    6120
tctgtccagc ctcagagttt aggttgttac cagatcaagt ccttatcttt gtgtccaact    6180
attaagtcag tgttttcttt ccaggccccc ttcaggttga gtgtccctgg acactgagga    6240
gccagagttc tggcctgggc tggttccttc cttcttcccc cacctcactc tgaagcgcac    6300
ccccaattta gttgcttagt tttctcagtc tcagaaacaa cagtctcagg ctgattccct    6360
gggtcctaaa gataactctc cttactgctt taatttctac tccctgttct tagcctgggc    6420
cctgatatag tttcaatgac tttaacttttt gataactctc attatacaag taacagctgc    6480
```

```
ccaacagaaa agaaattttg gaagaaaaca gaaatataaa gaagaaaatt aaaatcaccc      6540
ataatctcac caccctcaga caaccacttt taaacattta tgcttatttt ttccagatat      6600 ttttttgatgg gttcaaatca tgactcagct ctca                                 6634
```

<210> SEQ ID NO 6
<211> LENGTH: 176
<212> TYPE: PRT
<213> ORGANISM: Homo sapiens

<400> SEQUENCE: 6

```
Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

<210> SEQ ID NO 7
<211> LENGTH: 98
<212> TYPE: PRT
<213> ORGANISM: Homo sapiens

<400> SEQUENCE: 7

```
Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser
```